United States Patent
Ben Ezer et al.

(10) Patent No.: US 10,598,607 B2
(45) Date of Patent: Mar. 24, 2020

(54) OBJECTIVE LENS

(71) Applicant: Camtek Ltd., Migdal Ha'emek (IL)

(72) Inventors: Zehava Ben Ezer, Balfuria (IL); Menachem Regensburger, Shimshit (IL); Shimon Koren, Haifa (IL); Tomer Gilad, Kiryat Tivon (IL); Shy Shapira, Kiryat Tivon (IL)

(73) Assignee: Camtek Ltd., Migdal Haemeq (IL)

( * ) Notice: Subject to any disclaimer, the term of this patent is extended or adjusted under 35 U.S.C. 154(b) by 104 days.

(21) Appl. No.: 15/881,777

(22) Filed: Jan. 28, 2018

(65) Prior Publication Data

US 2019/0033234 A1 Jan. 31, 2019

Related U.S. Application Data

(60) Provisional application No. 62/519,497, filed on Jun. 14, 2017.

(51) Int. Cl.
| | |
|---|---|
| *G01N 21/95* | (2006.01) |
| *G01N 21/55* | (2014.01) |
| *H01L 21/66* | (2006.01) |
| *H01L 21/67* | (2006.01) |
| *G01N 21/956* | (2006.01) |

(52) U.S. Cl.
CPC ......... *G01N 21/9505* (2013.01); *G01N 21/55* (2013.01); *G01N 21/95623* (2013.01); *H01L 21/67276* (2013.01); *H01L 22/12* (2013.01); *G01N 2021/557* (2013.01); *G01N 2201/068* (2013.01); *G06T 2207/30148* (2013.01)

(58) Field of Classification Search
CPC ............... G01N 21/9505; G01N 21/55; G01N 2021/557; G01N 2201/068; H01L 21/67276; H01L 22/12; G06T 2207/30148
See application file for complete search history.

(56) References Cited

U.S. PATENT DOCUMENTS

| | | | |
|---|---|---|---|
| 2008/0204740 A1* | 8/2008 | Berg ...................... | G01B 11/16 356/239.2 |
| 2013/0148115 A1* | 6/2013 | Berlatzky ............ | G01N 21/956 356/237.5 |

* cited by examiner

*Primary Examiner* — Jamil Ahmed
(74) *Attorney, Agent, or Firm* — Reches Patents

(57) ABSTRACT

An inspection system for inspecting a semiconductor substrate, the inspection system may include an inspection unit that comprises a partially blocking bright field unit and a non-blocking bright field unit; wherein the partially blocking bright field unit is configured to block any specular reflection that fulfills the following: (a) the specular reflection is caused by illuminating, along a first axis, of an area of the wafer, (b) the specular reflection propagates along a second axis, (c) the first axis and the second axis are symmetrical about a normal to the area of the wafer, and (d) the normal is parallel to an optical axis of the partially blocking bright field unit; and wherein the non-blocking bright field unit is configured to pass to the image plane any specular reflection that fulfills the following: (a) the specular reflection is caused by illuminating, along the first axis, of an area of the wafer, (b) the specular reflection propagates along the second axis, (c) the first axis and the second axis are symmetrical about the normal, and (d) the normal is parallel to the optical axis of the partially blocking bright field unit.

23 Claims, 38 Drawing Sheets

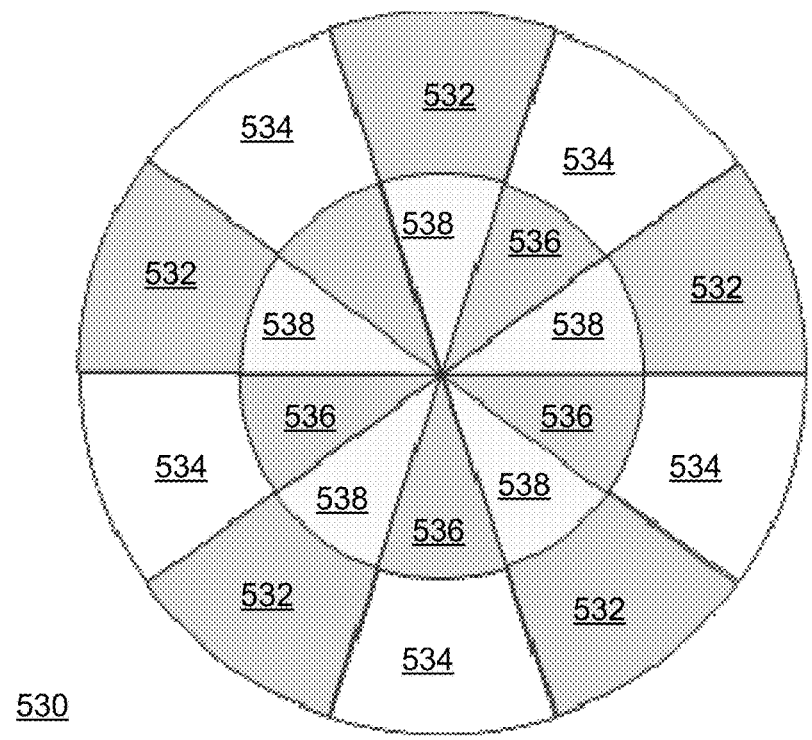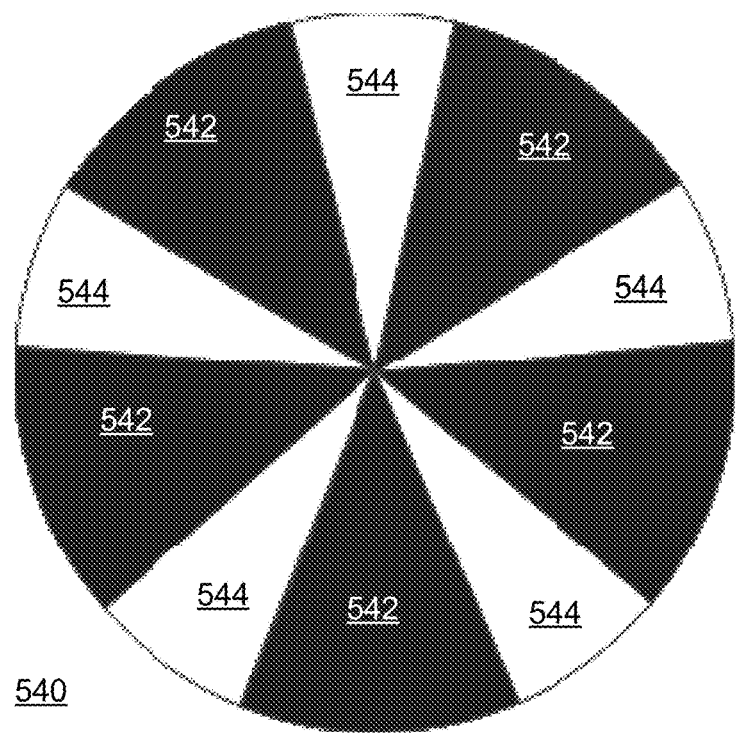
FIG. 14

Scanning a semiconductor substrate that has an upper layer that was manufactured by an epitaxial growth process to provide one or more images of one or more regions of the semiconductor substrate. The scanning is performed by the partially blocking bright field unit. 2710

Processing the one or more images to find locations that should have been flat – but are inclined 2720

Disqualifying, verifying, or performing measurements (metrology) of the locations that should have been flat – but are inclined. 2730

Scanning the external surface of one or more bonded wafers to provide one or more images of one or more regions of the external surfaces of the one or more bonded wafers. The scanning is performed by the partially blocking bright field unit. 2870

Processing the one or more images to find locations that should have been flat – but are inclined. These locations may be indicative of the internal defects – formed in the interface between bonded wafers. 2890

Scanning the external surface of a semiconductor substrate to provide one or more images of one or more regions of the external surface of the semiconductor substrate. One or more internal bumps are located between the semiconductor substrate and another semiconductor substrate. The scanning is performed by the partially blocking bright field unit.   3010

Processing the one or more images to find bump defects . 3020

Performing a first inspecting session that comprises inspecting a first region of a semiconductor substrate, wherein the inspecting of the first region comprises blocking, by a partially blocking bright field unit, any specular reflection that fulfills the following: (a) the specular reflection is caused by illuminating, along a first axis, of an area of the wafer, (b) the specular reflection propagates along a second axis, (c) the first axis and the second axis are symmetrical about a normal to the area of the wafer, and (d) the normal is parallel to an optical axis of the partially blocking bright field unit. 3110

Performing a second inspecting session that comprises inspecting a second region of the semiconductor substrate, wherein the inspecting of the second region comprises passing to an image plane any specular reflection that fulfills the following: (a) the specular reflection is caused by illuminating, along the first axis, of an area of the wafer, (b) the specular reflection propagates along the second axis, (c) the first axis and the second axis are symmetrical about the normal, and (d) the normal is parallel to the optical axis of the partially blocking bright field unit . 3120

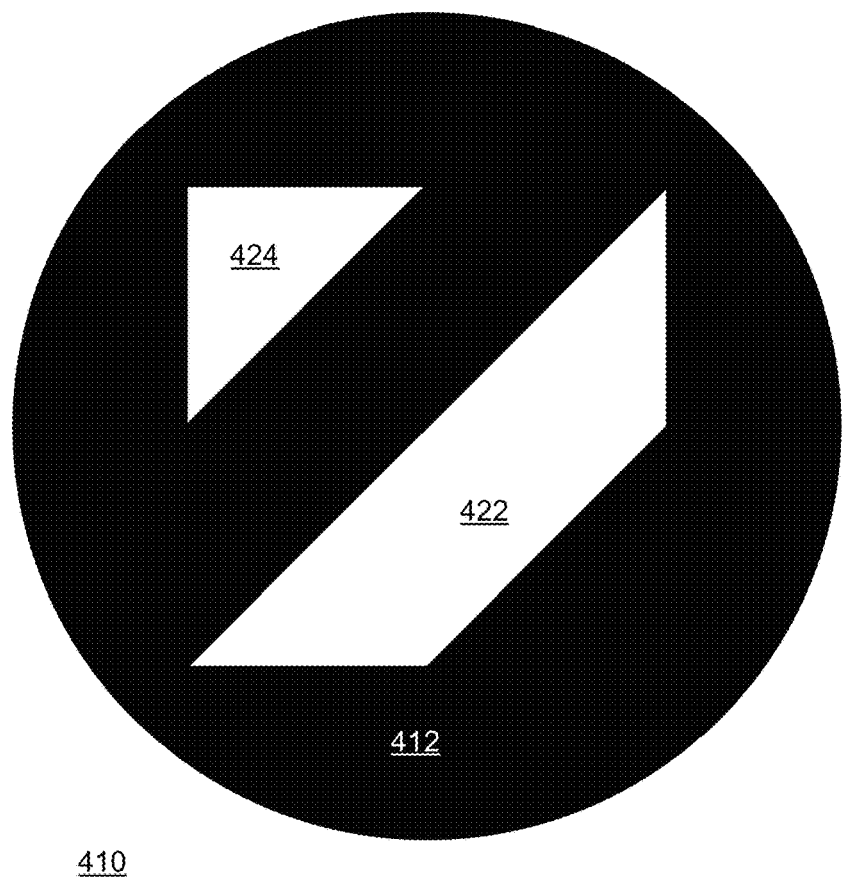
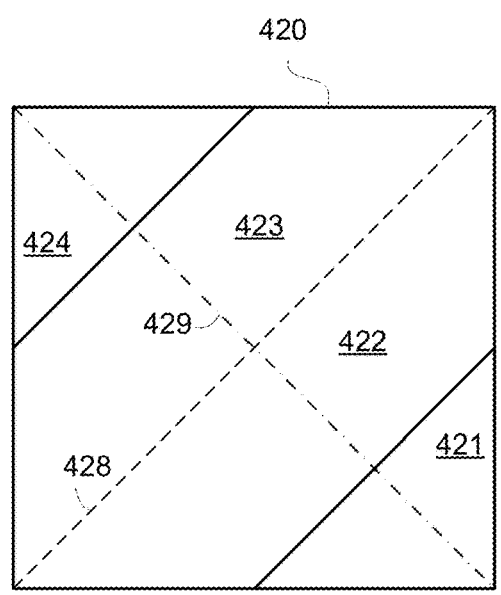
FIG. 32

450

450

450

OBJECTIVE LENS

BACKGROUND OF THE INVENTION

This application claims priority from U.S. provisional patent 62/519,497 having a filing date of Jun. 14, 2017 which is incorporated herein by reference.

BACKGROUND OF THE INVENTION

In recent years the complexity of electronic products—smartphones, tablets, automotive vehicles, IoT, etc., is growing while the demands on overall miniaturization of these systems remain. The thickness and dimensions of semiconductor chips are reduced from generation to generation while the content of the electronic functions is expected to grow. Semiconductor manufacturing uses different techniques to answer this demand: 2.5-D, 3DIC, "Advanced Packaging", Fanout wafer and substrate level packaging, integrating multiple electronic functions on one single silicon chip by methods such as System on Chip (SOC), new and efficient "Heterogeneous Integration" techniques, etc. One chip may integrate in one module a single to several advanced digital chips with various functions such as Digital RF, Analog, Power, Memory, Image Sensors and Microelectronic Mechanical Systems (MEMS).

Multichip modules incorporate different semiconductor chips from different processes that have no process correlation between them. Thus the deviation of performance of one chip embedded in the process, does not provide information on the process deviation of another chip.

A single low cost faulty chip can cause the failure of an expensive packaging module or of the final product. This vulnerability to failure is further aggravated by the fact that very few process steps in the advanced packaging module may be undone. Thus a faulty chip may not be removed after it has been embedded in an advanced packaging module.

Thus each die embedded in an advanced module needs to be tested and the advanced packaged module need to be tested as well, for visible external and internal defects (to rule out the existence of internal cracks that are usually formed during the die singulation process). Furthermore, discovering all hidden defects, is also important as a reliability measure. An undetected hidden defect, such as an internal crack or missing or defective internal bumps integrated between different layers, is in many cases NOT detectable by electrical test before product shipment. A hidden crack, may later, when the product is in the customers "hands", develop into an product failure. Such field failures are most financially damaging and therefore great efforts need to be taken to prevent them before shipment.

In the prior art systems in order to inspect, detect and measure inner layers defects in the substrate such as semiconductor wafers, expensive, time—consuming or destructive methods are used, such as X-Ray light imaging, IR or UV light imaging, SEM sampling of wafers cross-sections. In regular AOI techniques known in prior art, the inside layers' defects (such as side wall cracks) are invisible—resulting in significant losses to the end users.

Thus a high throughput and efficient AOI system and method are required to prevent field failures as described above. Such a high throughput detection system and method may also be required in other technologies not limited to "Heterogeneous Integration".

SUMMARY

There are provided systems, methods and non-transitory computer for evaluating semiconductor substrates as illustrated in the application.

Any combination of any steps of any method illustrated in the application may be provided.

Any combination of any units and/or components of any system illustrated in the application may be provided.

Any combination of any instructions stored in any non-transitory computer readable medium illustrated in the application may be provided.

BRIEF DESCRIPTION OF THE INVENTION

The present invention will be understood and appreciated more fully from the following detailed description taken in conjunction with the drawings in which:

FIG. 14 illustrates at least one example of at least one aperture stop;

FIG. 18 illustrates an example of a method;

FIG. 21 illustrates an example of a method;

FIG. 23 illustrates an example of a method;

FIG. 24 illustrates an example of a method;

FIG. 32 illustrates at least one example of at least one aperture stop;

DETAILED DESCRIPTION OF THE INVENTION

Figure 1:
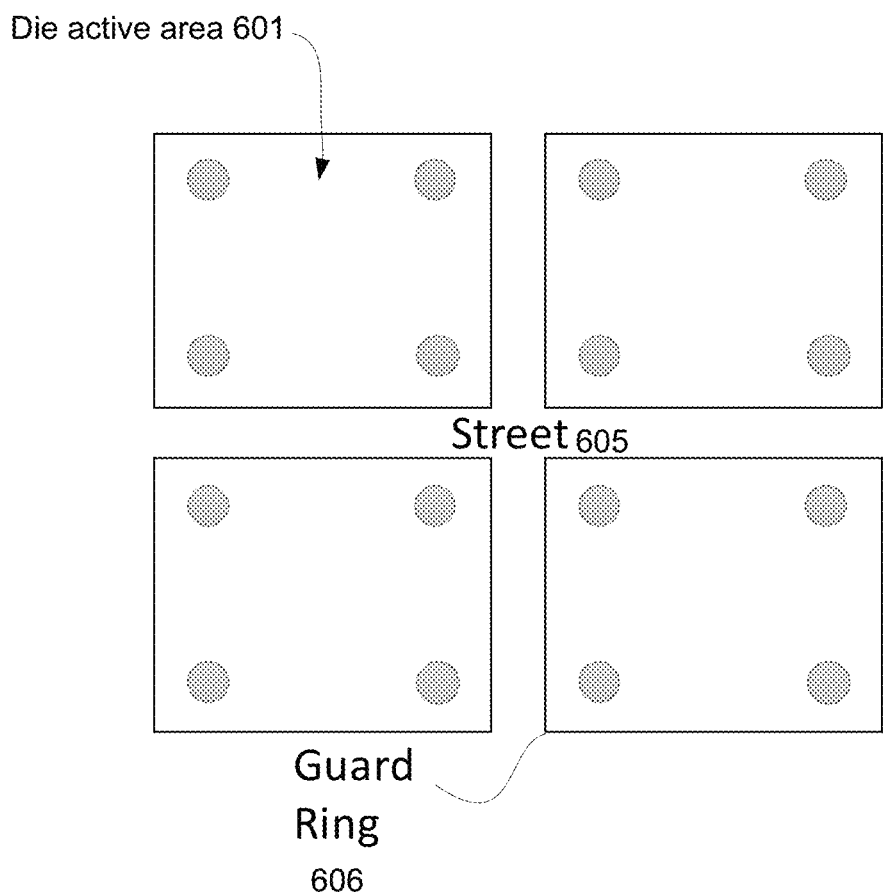
FIG. 1 illustrates an example of a diced wafer.

Any reference to a system should be applied, mutatis mutandis to a method that is executed by a system and/or to a non-transitory computer readable medium that stores instructions that once executed by the system will cause the system to execute the method. The system may be an inspection system, a verification system, a metrology system or a combination thereof.

Any reference to a method should be applied, mutatis mutandis to a system that is configured to execute the method and/or to a non-transitory computer readable medium that stores instructions that once executed by the system will cause the system to execute the method.

Any reference to a non-transitory computer readable medium should be applied, mutatis mutandis to a method that is executed by a system and/or a system that is configured to execute the instructions stored in the non-transitory computer readable medium.

The term "and/or" is additionally or alternatively.

The terms "comprising", "Consisting" and "consisting essentially of" are used in an interchangeable manner.

For example—a system that is illustrated as including certain units and/or components may (a) include additional units and/or components, (b) may include only the certain units and/or components, or (c) may include the certain units and/or components and additional units and/or components that do not materially affect the basic and novel characteristic(s)" of the claimed invention.

Yet for another example—a method that is illustrated as including certain steps may (a) include additional steps, (b) may include only the certain steps, or (c) may include the certain steps and additional steps that do not materially affect the basic and novel characteristic(s)" of the claimed invention.

Yet for another example—a non-transitory computer readable medium that is illustrated as storing certain instructions may (a) store additional instructions, (b) may store only the certain instructions, or (c) may store certain instructions and additional instructions that do not materially affect the basic and novel characteristic(s)" of the claimed invention.

Because the systems implementing the present invention is, for the most part, composed of optical components and circuits known to those skilled in the art, circuit details will not be explained in any greater extent than that considered necessary as illustrated above, for the understanding and appreciation of the underlying concepts of the present invention and in order not to obfuscate or distract from the teachings of the present invention.

In the following specification, the invention will be described with reference to specific examples of embodiments of the invention. It will, however, be evident that various modifications and changes may be made therein without departing from the broader spirit and scope of the invention as set forth in the appended claims.

The term "specular reflection" refers (wikipedia.org) to a mirror-like reflection of light from a surface, in which the direction of incoming light (the incident ray), and the direction of outgoing light reflected (the reflected ray) make the same angle with respect to the surface normal, thus the angle of incidence equals the angle of reflection ($\theta_i=\theta_r$ in the figure), and that the incident, normal, and reflected directions are coplanar.

Figure 37:
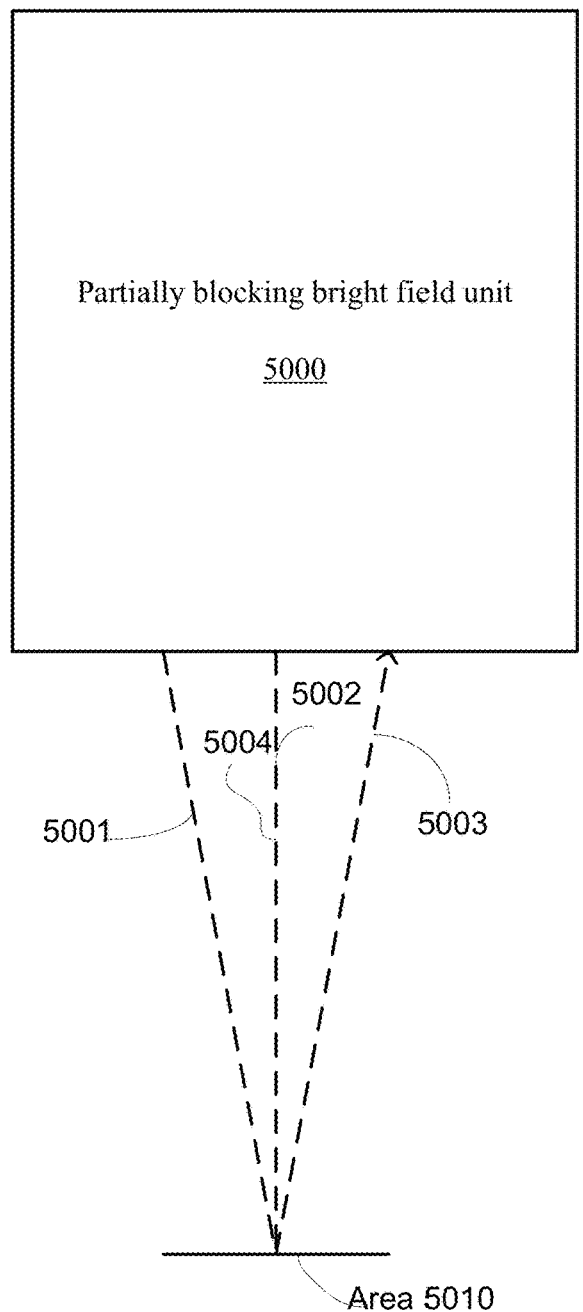
FIG. 37 illustrates an area of a semiconductor substrate and a partially blocking bright field unit.
Figure 38:
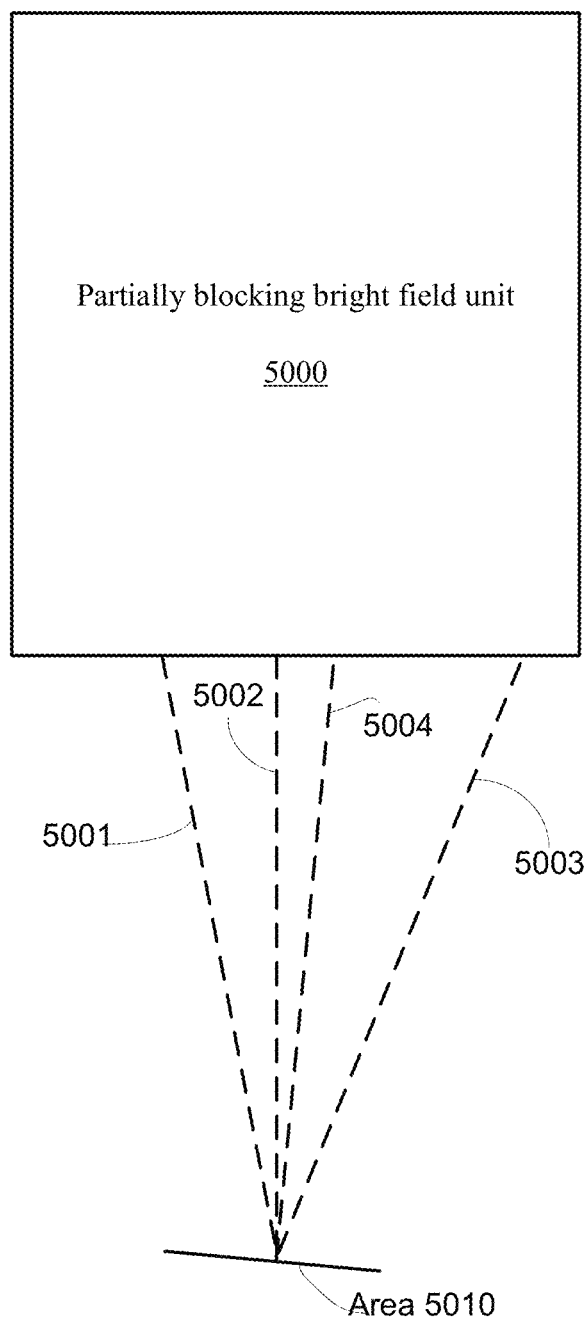
FIG. 38 illustrates an area of a semiconductor substrate and a partially blocking bright field unit.

A partially blocking bright field unit is unit that is configured to block any specular reflection that fulfills the following: (a) the specular reflection is caused by illuminating, along a first axis, of an area of the wafer, (b) the specular reflection propagates along a second axis, (c) the first axis and the second axis are symmetrical about a normal to the area of the wafer, and (d) the normal is parallel to an optical axis of the partially blocking bright field unit. In FIGS. 38 and 39 partially blocking bright field unit 5000 has an optical axis 5002, the normal (to area 5010) is 5004, the first axis is denoted 5001 (and represented a center of an impinging light beam, i.e. the illumination beam), and the second axis is denoted 5003 (and represents a center of the specular reflection). In FIG. 37 the area 5010 is horizontal and optical axis 5002 is vertical. In FIG. 38 area 5010 is oriented.

A non-blocking bright field unit is configured to pass to the image plane any specular reflection that fulfills the following: (a) the specular reflection is caused by illuminating, along the first axis, of an area of the wafer, (b) the specular reflection propagates along the second axis, (c) the first axis and the second axis are symmetrical about the normal, and (d) the normal is parallel to the optical axis of the partially blocking bright field unit.

The partially blocking bright field unit and/or the non-blocking bright field unit may pass or block one or more other light beams.

The partially blocking bright field unit and the non-blocking bright field unit are used for acquiring (or at least assisting in acquiring) one or more images of one or more semiconductor substrates.

The partially blocking bright field unit and the non-blocking bright field unit may include optical elements such as lenses, aperture stops, and the like.

The partially blocking bright field unit and the non-blocking bright field unit may or may not include light sources, and/or sensors, and the like.

There is provided a system and method that are fast, cost effective and non-destructive that allows to have Dark-field imaging within the Numerical Aperture of the Bright-filed optical and imaging channel.

There may be provided a system and method for automated optical inspection of different semiconductor substrates related to semiconductor industry such as patterned semiconductor wafers and substrates, non-patterned semiconductor wafers and substrates, diced semiconductor substrates, non-diced semiconductor substrates, dies of any one of the semiconductor wafers, etc., pattern recognition techniques, defect detection, verification, metrology and similar.

Some of the following examples refer to a wafer. This is merely a non-limiting example of a semiconductor substrate.

Some of the examples refer to light and especially light pulses. It should be noted that light is a non-limiting example of radiation and that any reference to light may be applied mutatis mutandis to other types of radiation such as infrared, near infrared, ultra violet, deep ultraviolet, and the like.

FIG. 1 illustrates an example of four active dies regions (such as 601) that are spaced apart by streets (such as 605). In each die the active die region is surrounded by a redundant die region. The redundant die regions form the streets. The border between each active region and the redundant die region is known as guard ring 608.

The wafer will be diced to provide a diced wafer that includes spaced apart dies. The dicing process included mechanically removing the centers of the streets—these centers are known as kerf.

Figure 2:
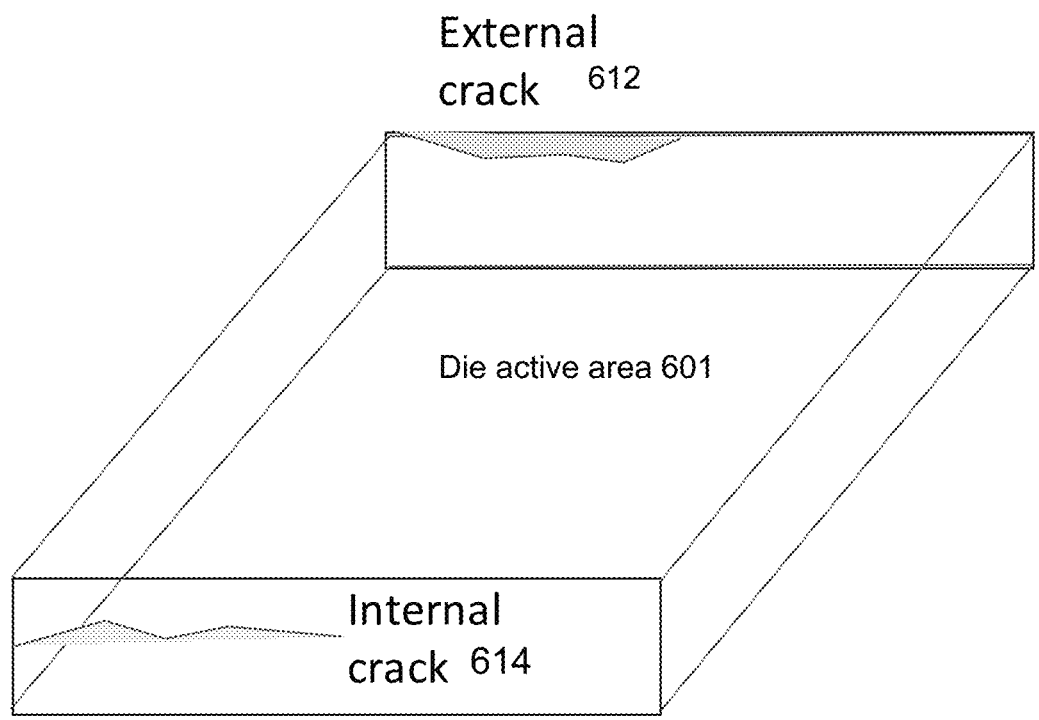
FIG. 2 illustrates an example of a defective die of a diced wafer.

Internal cracks and external cracks may be formed during the dicing process. FIG. 2 illustrates external crack 612 that appears on the upper surface of the die active region, and also illustrated an internal crack 614 formed in the die active region.

Figure 3:
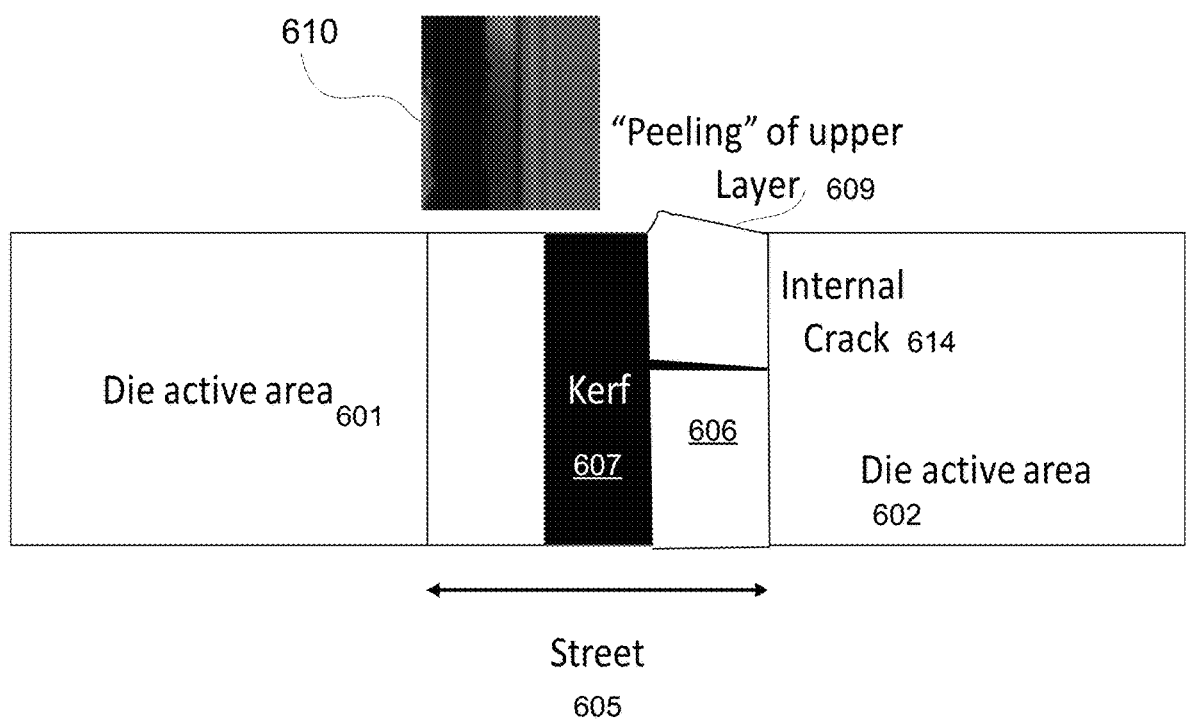
FIG. 3 illustrates an example of defective dies of a diced wafer.

FIG. 3 illustrates a cross section of two die active regions 601 and 602, an internal crack 614 that forms an upper layer deformation 609 (in the form of a peeling of the upper layer). Most of the internal crack 614 is formed in the redundant die region 606—but a part of the internal crack 614 is formed in the die active area 602.

FIG. 3 also illustrates kerf 607, street and an image 610 of the upper layer deformation 609.

Figure 4:
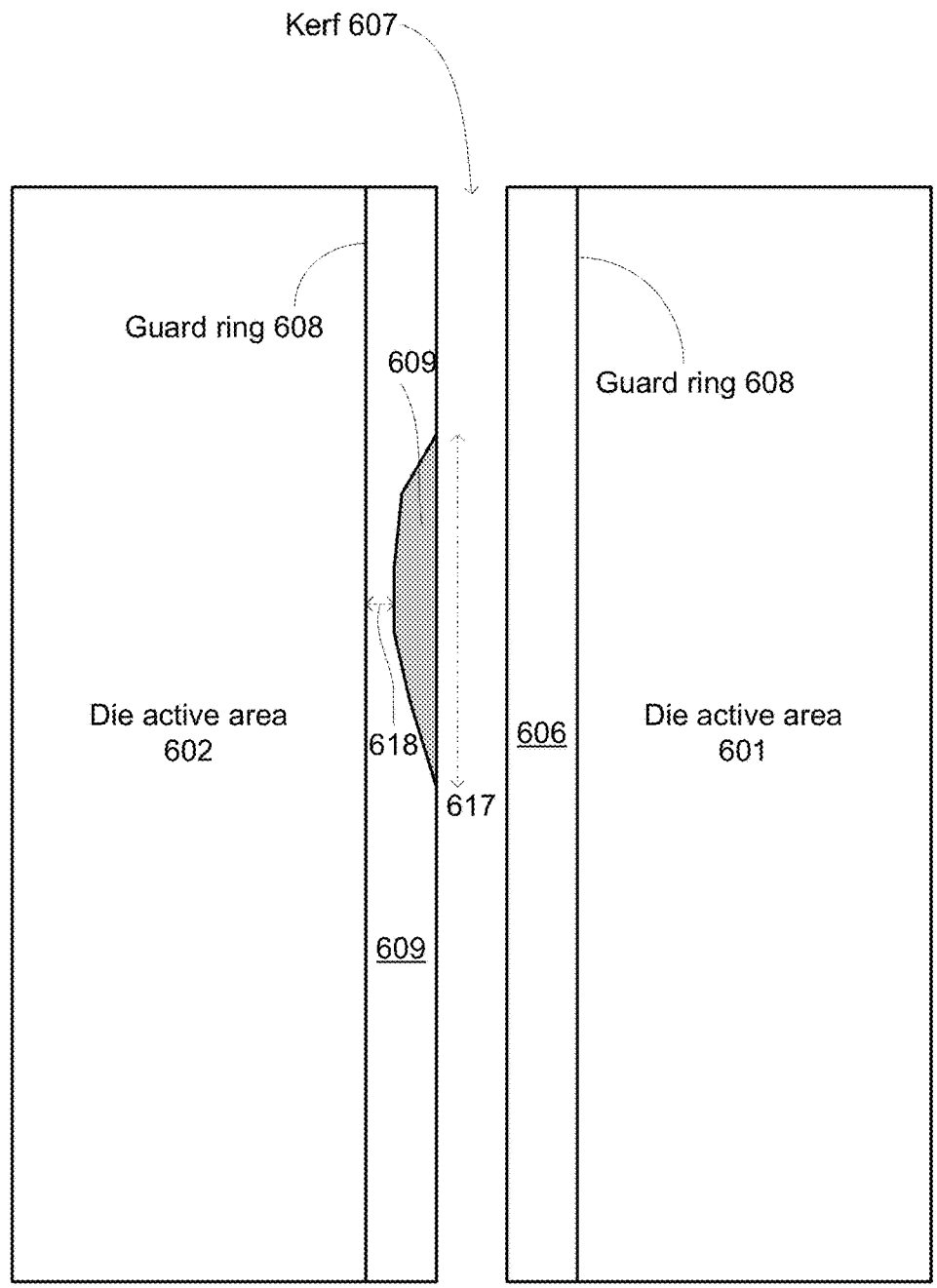
FIG. 4 illustrates an example of defective dies of a diced wafer.

FIG. 4 illustrates a top view of two die active regions 601 and 602, an upper layer deformation 609 (such as peeling). Most of the internal crack 614 is formed in the redundant die region 606—but a part of the internal crack 614 is formed in the die active area 602.

FIG. 4 also shows guard rings 608, kerf 607.

FIG. 4 further shows the length 617 of the upper layer deformation 609 and the minimal distance 618 between the upper layer deformation 609 and the guard ring. It should be noted that other metrics may be used to evaluate the potential harm of the crack. Non-limiting example of metrics may include the area of the upper layer deformation, the area between the upper layer deformation and the guard ring, and the like.

Figure 5:
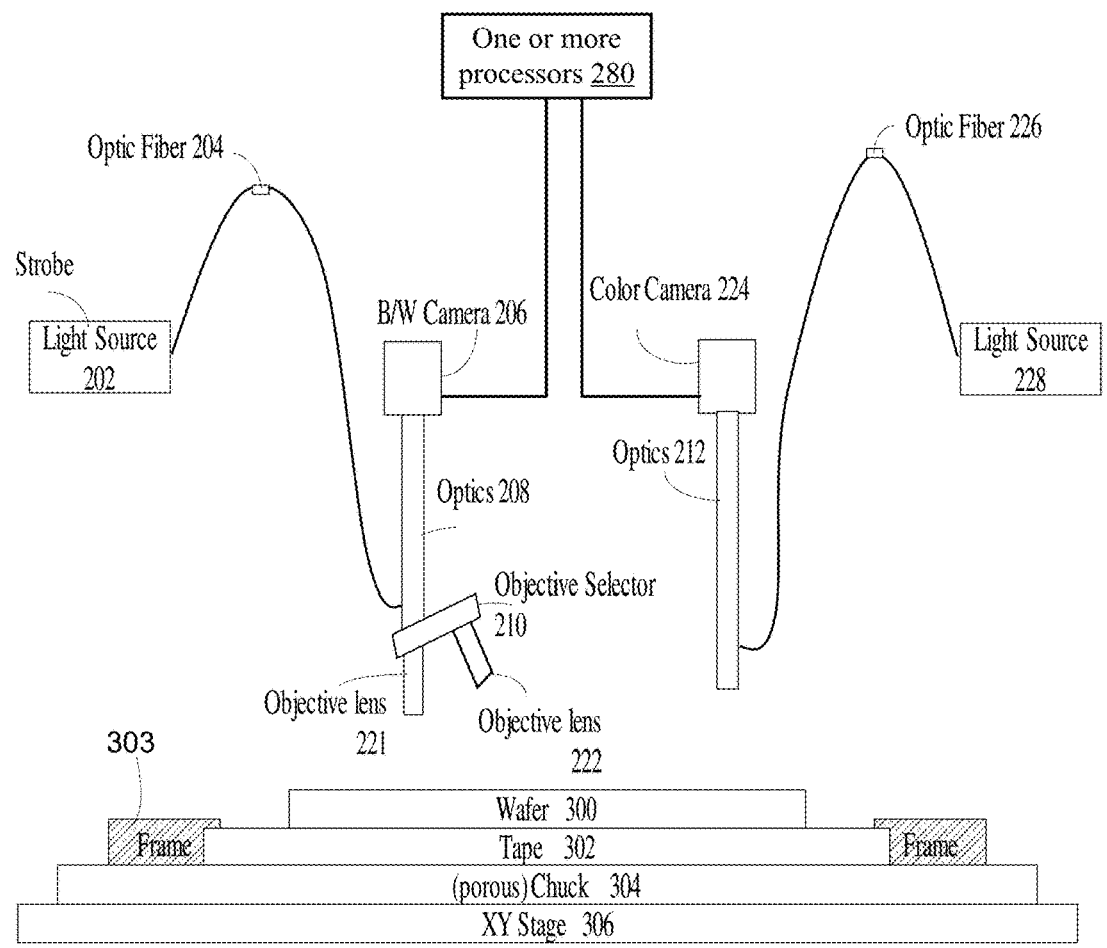
FIG. 5 illustrates an example of a semiconductor substrate and a system.

FIG. 5 illustrates a system 200 and a diced wafer 300.

System 200 has a verification unit, and an inspection unit.

The inspection unit may include a non-blocking bright field unit and a partially blocking bright field unit.

The partially blocking bright field unit may be incorporated in an objective changing apparatus—210—objective selector (such as a linear or rotating turret) that allows to automatically change the objectives or field blocking stops.

Thus, it enables on one machine a sequence of partially blocking bright field inspection for inner cracks and non-blocking bright field inspection for other defects on die or for different magnifications of the imaging surface.

The partially blocking bright field unit is configured to block any specular reflection that fulfills the following: (a) the specular reflection is caused by illuminating, along a first axis, of an area of the wafer, (b) the specular reflection propagates along a second axis, (c) the first axis and the second axis are symmetrical about a normal to the area of the wafer, and (d) the normal is parallel to an optical axis of the partially blocking bright field unit. The partial blocking may be achieved by using one or more aperture stops.

The first axis and the second axis may correspond to the middle of the illumination beam and specular reflection respectively.

The non-blocking bright field unit is configured to pass to the image plane any specular reflection that fulfills the following: (a) the specular reflection is caused by illuminating, along the first axis, of an area of the wafer, (b) the specular reflection propagates along the second axis, (c) the first axis and the second axis are symmetrical about the normal, and (d) the normal is parallel to the optical axis of the partially blocking bright field unit.

The non-blocking bright field unit may or may not have within the collection path and/or the illumination path any filters and/or polarizers or any other blocking filters.

The partially blocking bright field unit may be a microscope where the angles of impinging dark field illumination are contained within the numerical aperture (NA) of the microscope bright field imaging optics.

The non-blocking bright field unit and the blocking bright field unit may share some components—or may not share any component.

The inspection system may include a processor for processing images to identify any one of the following: inner cracks or bumps defects or epi pillar defects or bonded wafers inner layers defects or metrology (length, width, area calculations) of the identified inclination area above the planar surface inspected. Alternatively, a least some of the processing are executed by a processor located outside the system.

It shall be noted, that the inclination angle of the roughness above the planar surface inspected is well detected by the suggested systems and methods, when the angle of inclination is between 1° (1 degree) to 2° (2 degrees), however, the roughness detected by the suggested systems and methods may have smaller than 1° angle of inclination or larger than 2°.

The non-blocking bright field unit and the blocking bright field unit can share optics and black and white camera 206—and differ from each other by their objective lens—first objective lens 221 belongs to the partially blocking bright field unit (and may be referred to as a partially blocking objective lens), while second objective lens 222 belongs to the non-blocking bright field unit (and may be referred to as a non-blocking objective lens). The detector, which is the camera 206 may be an area camera such as CCD or CMOS digital video camera or a line camera such as TDI and others, it may be a grey-level (black and white camera or a color camera.

System 200 is illustrated as including an objective selector for selecting which objective lens (out of first objective lens 221 and second objective lens 222) to position in the collection path and the collection path of the inspection unit.

It should be noted that instead of replacing the objective lens, system 200 may include a configurable aperture stop—such as a configurable spatial light modulator (SLM)—that may be set to a partially blocking configuration and may also be set to a non-blocking configuration.

The SLM may be set to affect any property of the impinging light and/or the reflected light—(not just block or unblock the light)—for example—the SLM may be configured to apply the following functions—fully blocking, fully transparent, partially transparent, polarizing, rotating polarization, phase changing. Any reference to blocking or unblocking should be applied mutatis mutandis to any of these operations.

When the configurable SLM is configured in the partially blocking configuration then inspection unit operates as a partially blocking bright field unit.

When the configurable SLM is configured in the non-blocking configuration then inspection unit operates as a non-blocking bright field unit.

The configuration of the SLM may be changed in a dynamic manner—between one scan to another, or during the same scan, "on the fly", and the like. The change of the configuration of the SLM may be determined based on actual or expected properties of the areas to be scanned. The actual or expected properties of the areas to be scanned may be determined based on at least one out of design information (for example—computer aided design CAD files), results of previous scans of similar semiconductor substrates, and the like. The expected properties may include expected geometry, roughness, grids, and the like. The properties may defined which reflections to block and which reflections to pass, which phase shifts and/or polarization changes to induce—at various areas of the SLM.

The SLM may be a liquid crystal mask that can change "on the fly" an opaqueness of different regions to detect different angles of an inclinations beyond the planar substrate surface.

The SLM may dynamically change its blocking pattern. Thus, it can be used in applications where the desirable angle of inclination (with respect to the horizontal plane) may be selected electronically by changing the pattern. Thus, one can change the angles per job to fit to the actual inspected regions with different surface roughness. Tuning can be done during single scan or iteratively scan after scan.

For example—the system may scan one or more region of a semiconductor substrates when the SLM is set according to a first configuration and then scan one or more other regions of the semiconductor substrates (or may scan the same region with different configurations of the SLM).

If, for example, the system is looking for defects that have two facets—one configuration of the SLM may be used to detect the first facet and the second configuration of the SLM may be used to detect the second facet. The second configuration may applied only on location in which the first facet was detected—thereby saving time.

The semiconductor substrate may be a diced wafer. Dies that are spaced apart from each other and are supported by tape 302 that is held by frame 303. The frame 303 is supported by chuck 304 that can be moved by XY stage 306.

The inspection unit includes a light source 202 that may feed light pulses (triggered by strobes) through optic fiber 214 through optics 208 and first objective lens 221 towards diced wafer 300.

Optics 208 may include a beam splitter that may direct the light pulses from optic fiber 2014 towards diced wafer 300.

Light pulses reflected from the diced wafer 300 may be directed (either partially blocked on not blocked) through first objective lens 221, optics 208 to a black and white camera 206.

The blocking of the light depends on the configuration of the inspection unit—as a partially blocking or as non-blocking.

The inspection unit includes a light source 202 that may feed light pulses (triggered by strobes or by any other trigger) through optic fiber 214 through optics 208 and first objective lens 221 towards diced wafer 300.

The light source 202 may be any source of electromagnetic radiation such as laser, fiber, lamp, LED, Xenon, Strobe light, halogen, it could be of different wavelengths such as visible light spectrum or UV spectrum, IR spectrum or near IR spectrum. Light Source may include a polarizer or a spectrum filter.

The optic fiber is merely a non-limiting example of a light conduit. Any other light conduit and/or optical components may be used in the system.

Optics 208 may include a beam splitter that may direct the light pulses from optic fiber 204 towards diced wafer 300.

Light reflected from the diced wafer 300 may be directed (either partially blocked on not blocked) through first objective lens 221, optics 208 to a black and white camera 206.

The verification unit includes light source 228, optics 212, color camera 224, and optic fiber 226.

The light source 228 may feed light pulses (that may be triggered by a strobe controller, or defined in the light source itself) through optic fiber 226 through optics 212 towards diced wafer 300. Optics 212 may include an objective lens.

Optics 212 may include a beam splitter that may direct the light pulses from optic fiber 226 towards diced wafer 300.

Light reflected from the diced wafer 300 may be directed through optics 212 to color camera 224.

The black and white camera 206 may have a higher throughput than the color camera.

The verification unit may be directed only to suspected defected detected by the inspection unit—but this is not necessarily so.

The verification unit may detect the upper layer deformation 609 (in the form of a peeling of the upper layer)—as the peeling are of different color than their surroundings.

FIG. 5 also illustrates one or more processors 280 that may be configured to process detection signals received from any one of the inspection unit or verification unit and apply various inspection algorithms and/or verification algorithms such as but not limited to the methods illustrated in the application. The detection signals may be arranged in frames (for example by a frame grabber)—or may be fed to the one or more processors in any other manner.

The one or more processors may include one or more hardware processors. The same processor may be coupled to black and white camera 206 and also to the color camera. Alternatively, a different processor is allocated per each camera. There may be any number of cameras of each type and any number of processors associated with these cameras.

The one or more processors may also be configured to execute metrology algorithms and act (with any illumination and collection optics) as a part of a metrology unit.

Figure 6:
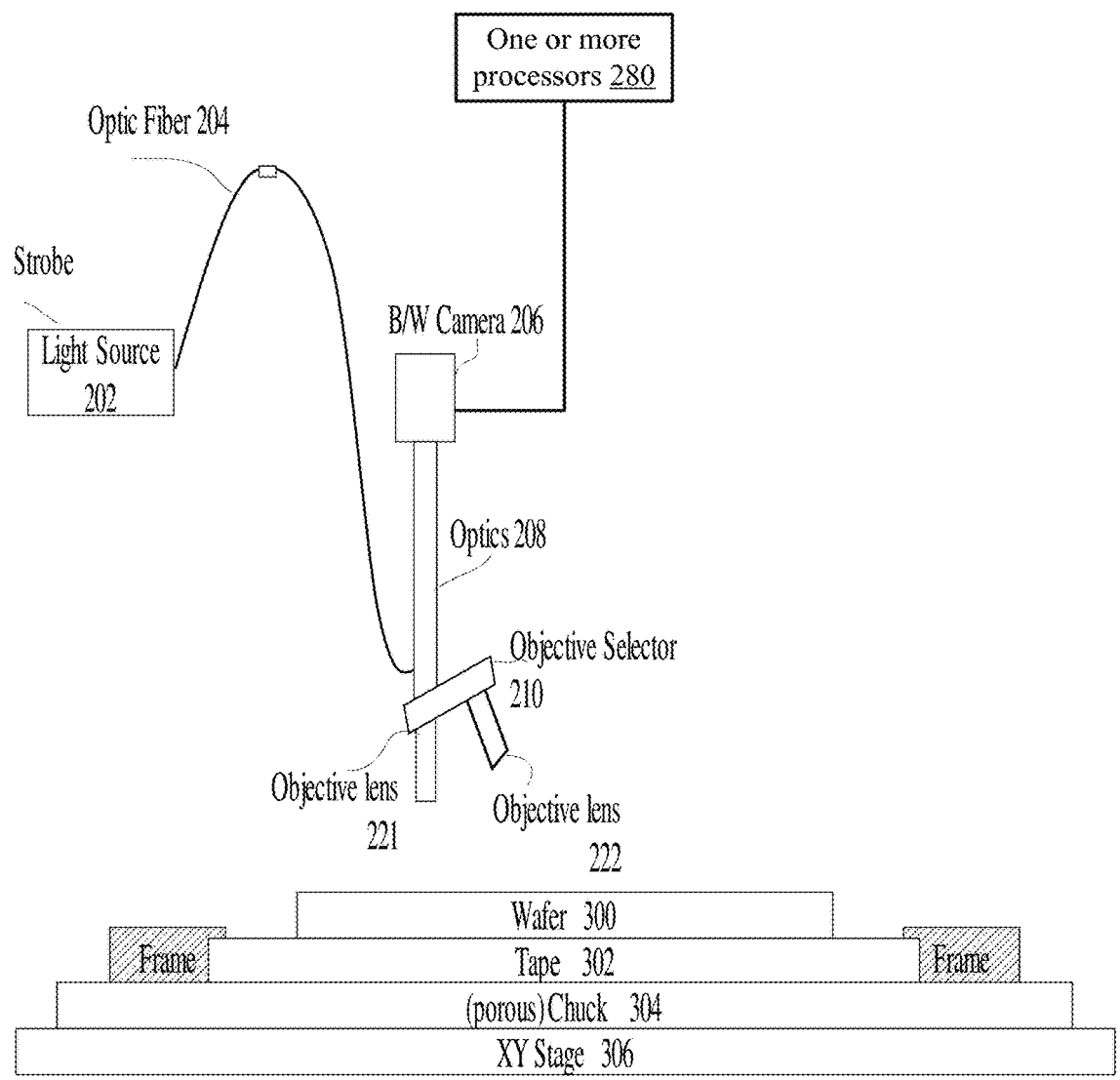
FIG. 6 illustrates an example of a semiconductor substrate and a system.

FIG. 6 illustrates a system 201 and diced wafer 300.

System 201 has an inspection unit—but differs from system 200 of FIG. 5 by a lack of a verification unit.

Figure 7:
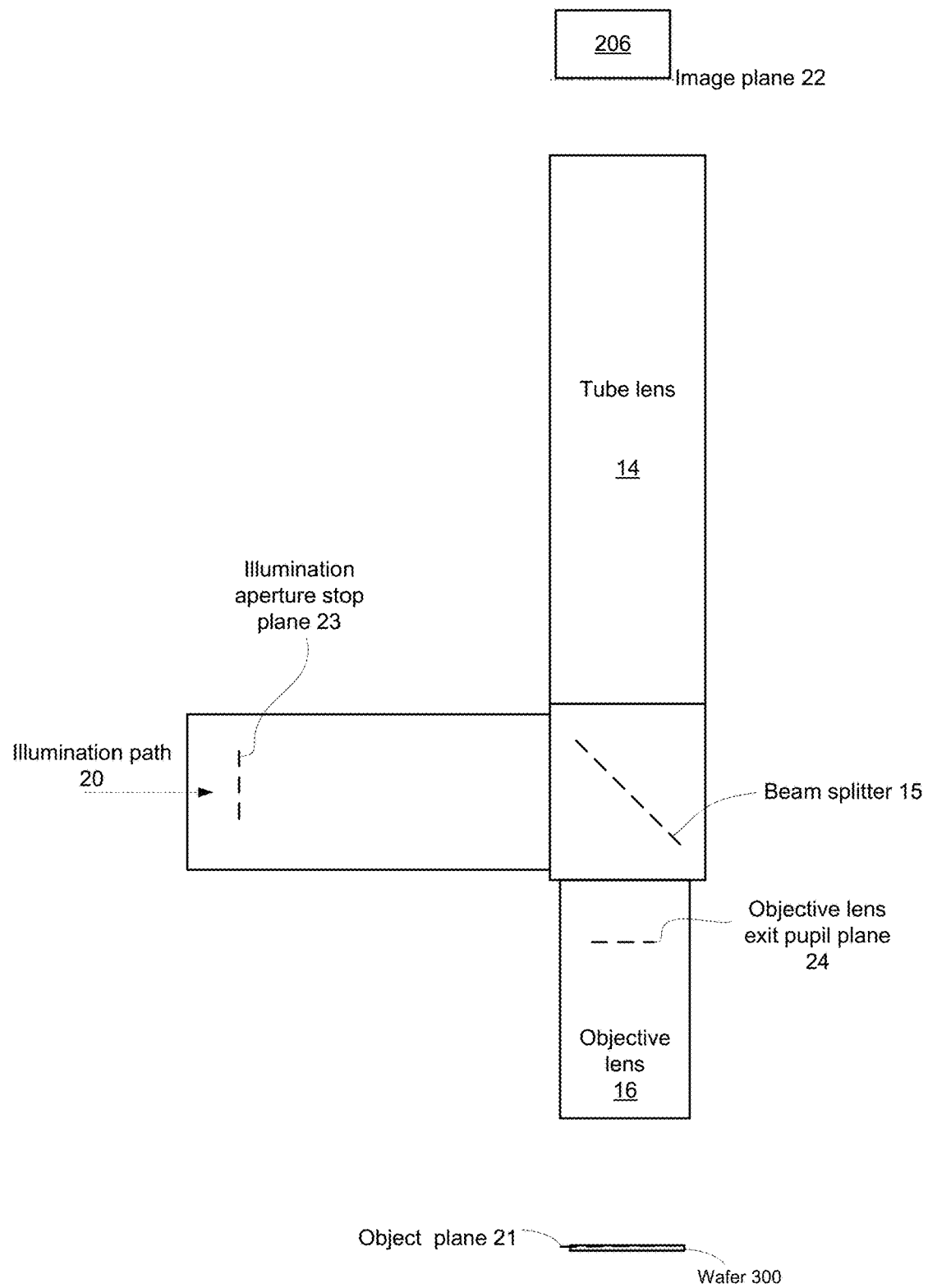
FIG. 7 illustrates an example of an inspection unit.
Figure 9:
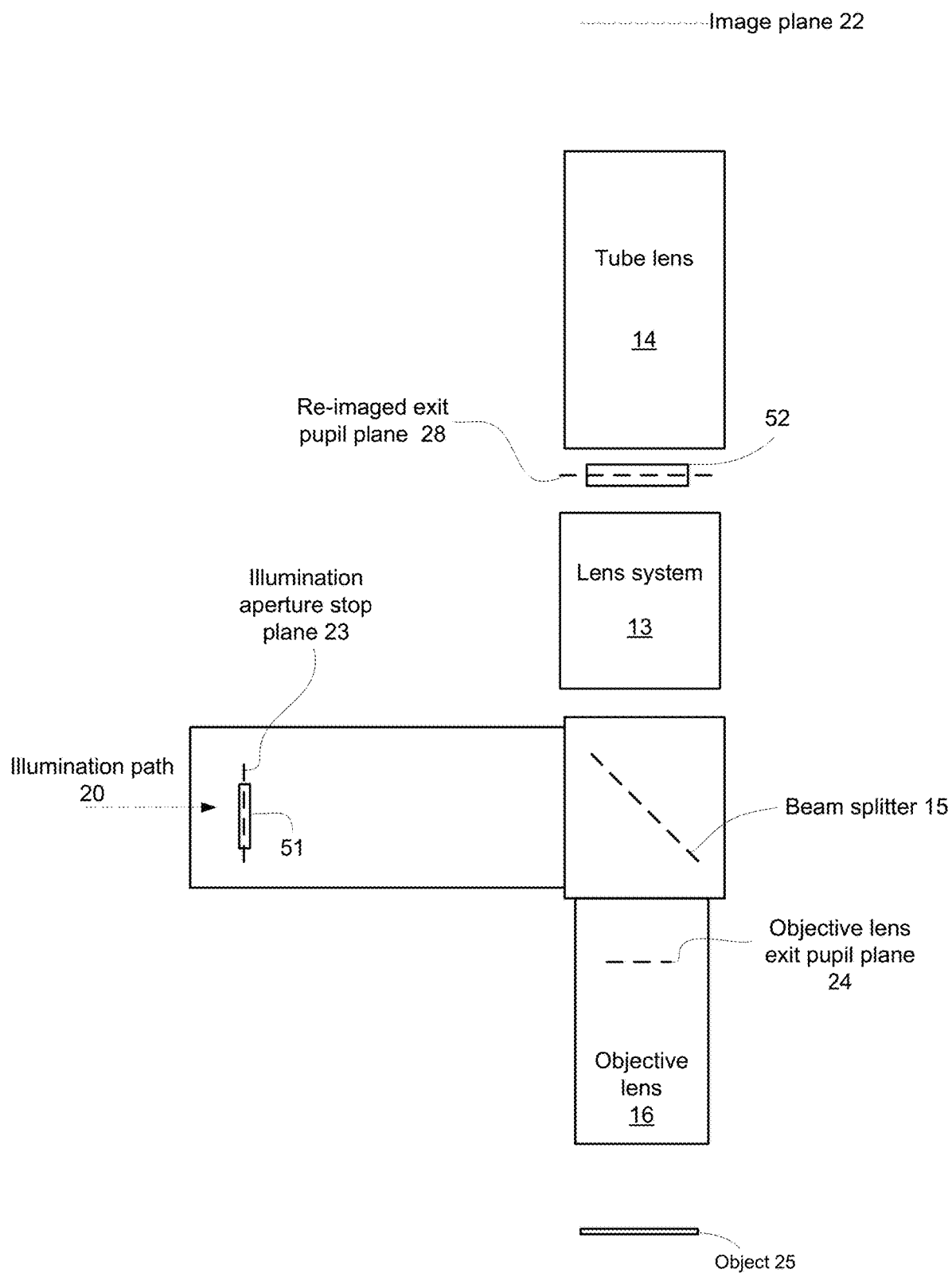
FIG. 9 illustrates an example of an inspection unit.
Figure 10:
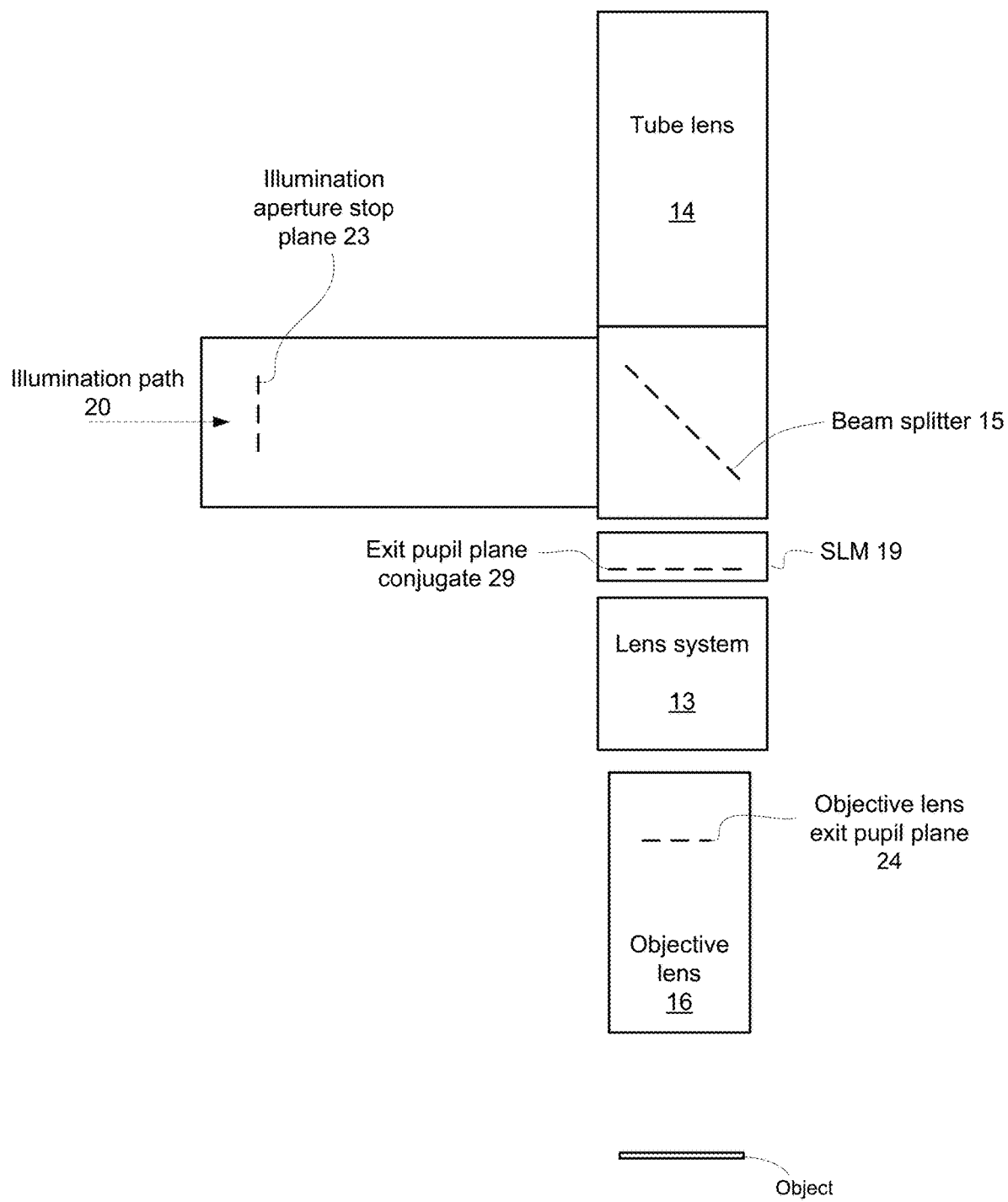
FIG. 10 illustrates an example of an inspection unit.

FIGS. 7, 9 and 10 illustrate various configurations of the inspection unit of either one of systems 200 and 201.

In FIG. 7, light pulses arrive from an illumination path 40 (for example—from optic fiber 204) pass through an illumination aperture stop plane 23 progress towards beam splitter 15, are directed (by beam splitter 15) towards objective lens exit pupil plane 24 and through objective lens 16 and onto diced wafer (not shown) that is located in object plane 21.

Light from the diced wafer passes through objective lens (and through objective lens exit pupil plane 24) through beam splitter 15, towards tube lens 14 and onto black and white camera (not shown) located within image plane 22.

In FIG. 7 the aperture stop may be positioned in the objective lens exit pupil plane 24. The objective stop may be a non-blocking aperture stop, a partially blocking aperture stop, may be a configurable objective stop that is set to a partially blocking configuration, or may be a configurable objective stop that is set to a non-blocking configuration.

FIG. 7 also illustrates a semiconductor substrate (such as wafer) 300 that is located in the object plane 21 and a black and white camera 206 that is located in the image plane 22.

It should be noted that a single aperture stop may be replaced by a group of aperture stops. The affect of the single aperture stop may be achieved by using the group of aperture stops. Examples of different groups of aperture stops are illustrated in some of the following figures.

Figure 8:
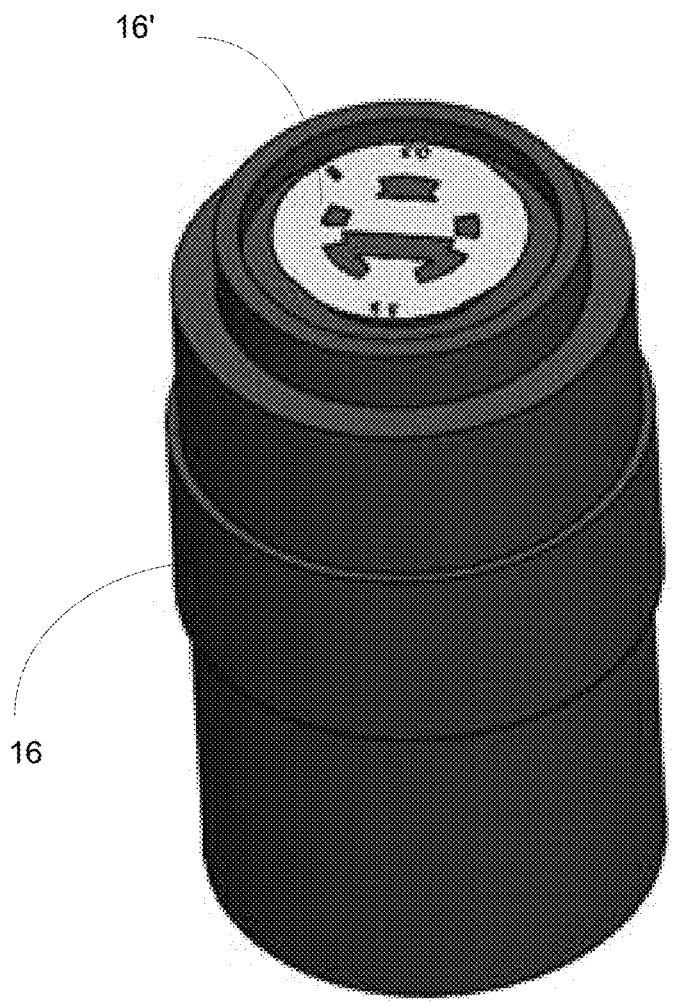
FIG. 8 illustrates an example of an aperture stop and an objective lens.

FIG. 8 illustrates an objective lens 16 and an aperture stop 16' that is located at an exit pupil of the objective lens—near the interface between the objective lens and the FIG. 9 is an example of an inspection unit that includes a group of aperture stops—the group includes first aperture stop and a second aperture stop.

The first aperture stop 51 is positioned in the illumination aperture stop plane 23 while the second aperture stop 52 is located at a re-imaged exit pupil plane 28. Re-imaged exit pupil plane 28 is located at the collection optics (for example between lens system 13 and tube lens 14)—and is positioned where the objective lens exit pupil plane 24 is imaged.

The first and/or second aperture stops may be static, may be moved in relation to each other, may move in relation to the object or any part of system 200.

FIG. 10 illustrates a SLM 19 that is positioned at the exit pupil plane conjugate 29. The exit pupil plane conjugate 29 is conjugate to illumination aperture stop plane 23. As indicated above—SLM 19 is configurable and may be set to a partially blocking configuration and may also be set to a non-blocking configuration.

The objective lens may be designed to have a free access to the objective lens exit pupil plane in a way that the aperture stop may be mechanically inserted in place or taken out from path to enable non-blocking bright field imaging.

The mechanical mount of special shape stop may adjustment means to position the stop precisely concentric with the lens optical axis The stop mount may include several different stop shapes to be exchanged according to an actual defect detection requirement.

Exchanging between the different stops may be motorized and automatically controlled.

Figure 11:
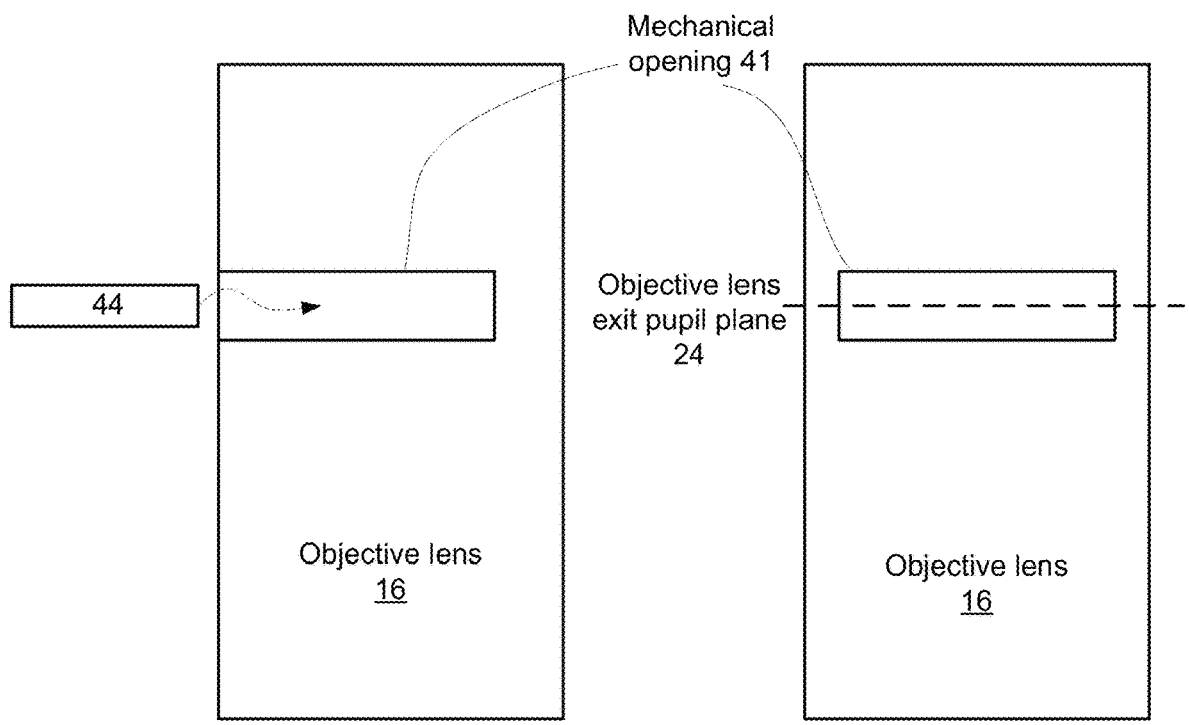
FIG. 11 illustrates an example of an objective lens.

FIG. 11 illustrates a side view and a front view of objective lens 16. FIG. 11 illustrates that the aperture stop 44 may be replaced by removing another aperture stop and inserting aperture stop 44 (though mechanical opening 41 formed in the objective lens). In FIG. 11 the aperture stop is positioned in the objective lens exit pupil plane 24.

Figure 12:
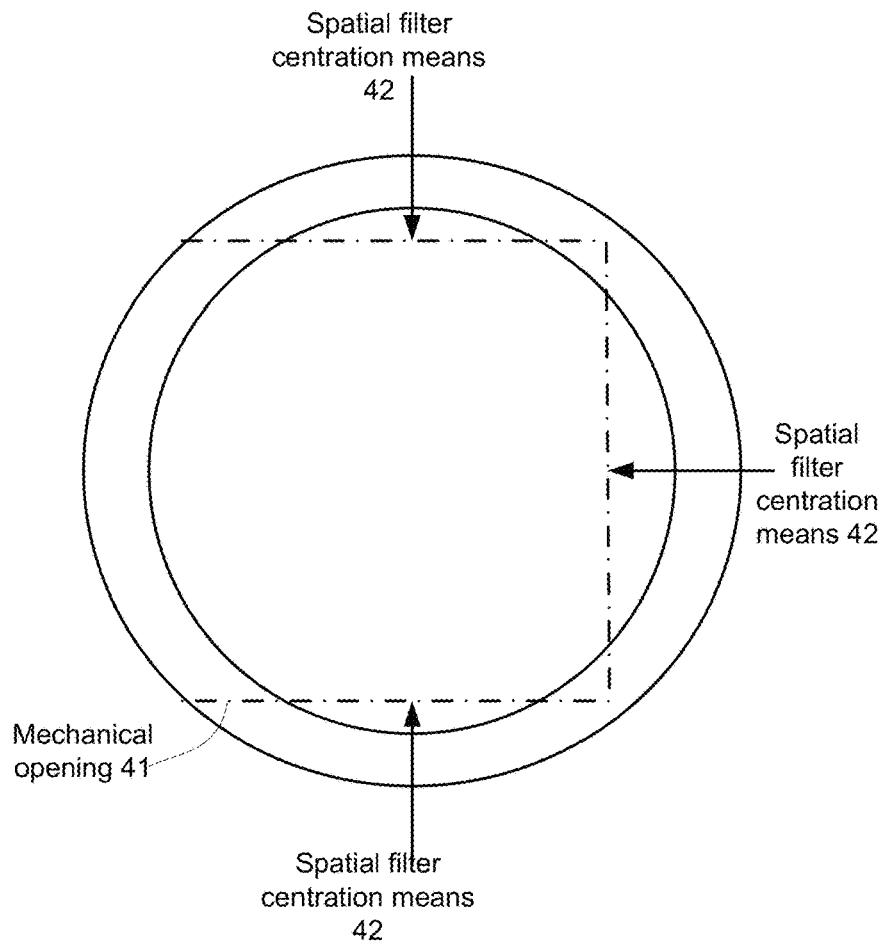
FIG. 12 illustrates an example of an objective lens.

FIG. 12 is a top view that illustrates that the objective lens may include spatial filter concentration means 42 for accurately positioning the aperture stop in the mechanical opening 41. The spatial filter concentration means 42 may include any mechanical means that can position the aperture stop in a controlled manner—they may include rails, bolts, recesses, screws, bolts, motors, controllers, monitoring unit for monitoring the position of the aperture store, and the like.

Figure 13:
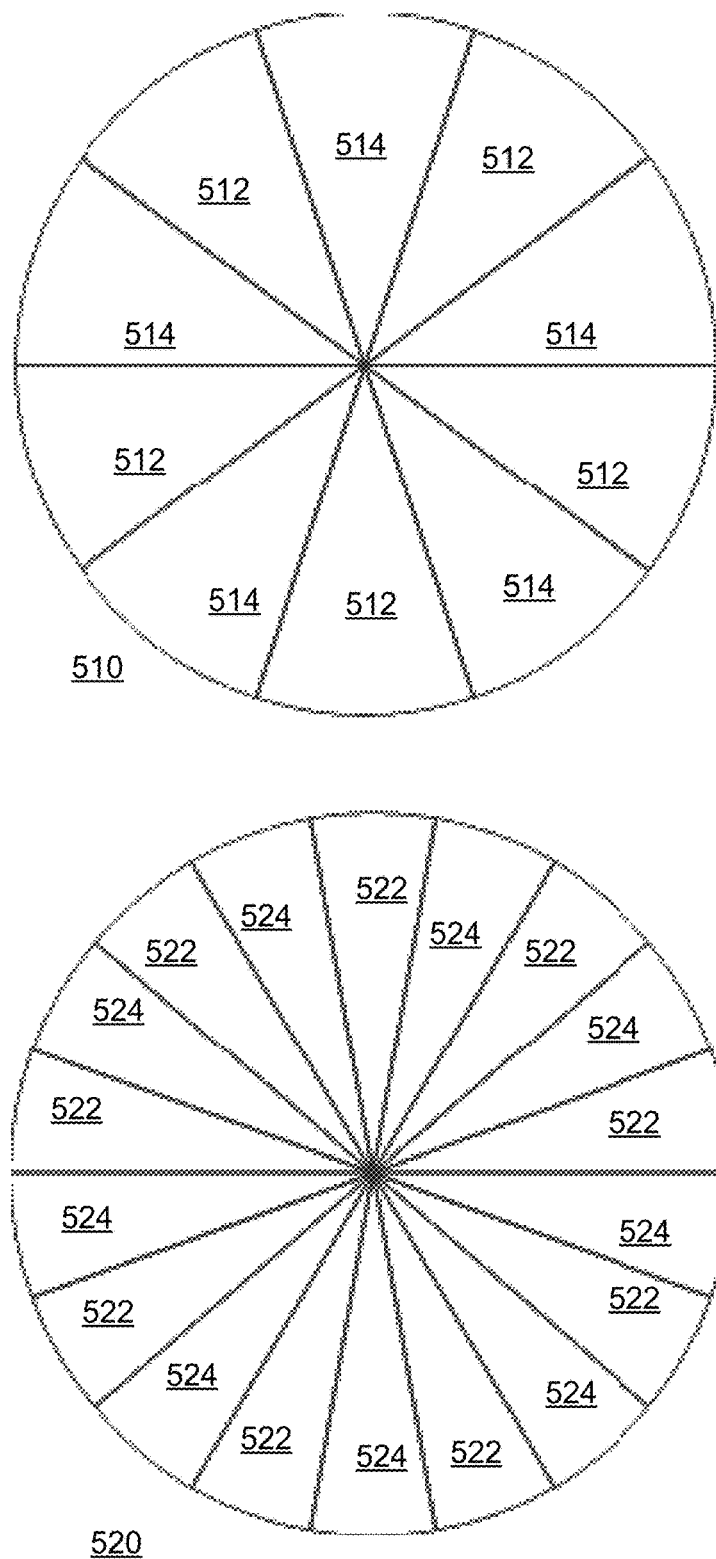
FIG. 13 illustrates at least one example of at least one aperture stop.

FIGS. 13 and 14 illustrate various example of a partially blocking aperture stop.

The partially blocking aperture stop may include segments of different types—such as first type segments and second type segments.

The first type segments may differ by polarization direction from the second type segments. Light of a first polarization will pass through the first type segment and does not pass through the second type segment. Light of a second polarization will pass through the second type segment and does not pass through the first type segment.

Additionally or alternatively, the first type segments may differ by spectral transmission from the second type segments. Light of a first spectrum will pass through the first type segment and does not pass through the second type segment. Light of a second spectrum will pass through the second type segment and does not pass through the first type segment.

Additionally or alternatively, the first type segments may differ by intensity transmission from the second type segments, where first type is transparent and second type is opaque.

FIG. 13 illustrates a partially blocking stop aperture 510 that includes ten segments that are shaped as slices (sectors)—including five first type segments 512 and five second type segments 514—that are arranged in an alternating manner. Each first type segment is surrounded by a pair of second type segments. Each second type segment is surrounded by a pair of first type segments.

FIG. 13 also illustrates a partially blocking stop aperture 520 that includes twenty segments that are shaped as slices (sectors)—including ten first type segments 522 and ten second type segments 524—that are arranged in an alternating manner.

It has been found the partially blocking stop aperture 520 improves sensitivity for lower angular deviation from optical axis in comparison to partially blocking stop aperture 510.

It should be noted that the number of the segments may differ than five or ten.

FIG. 14 illustrates a partially blocking stop aperture 530 that includes an inner circular region and an outer annular region. The inner circular region is surrounded by the outer annular region.

The inner circular region includes ten segments that are shaped as slices (sectors)—including five first type segments 536 and five second type segments 538—that are arranged in an alternating manner. Each first type segment is surrounded by a pair of second type segments. Each second type segment is surrounded by a pair of first type segments.

The outer annular region is segmented to ten segments—by imaginary radial lines the define the borders of the ten segments of the inner circular region. The ten segments include five first type segments 532 and five second type segments 534—that are arranged in an alternating manner. Each first type segment is surrounded (on both sides) by a pair of second type segments. Each second type segment is surrounded (on both sides) by a pair of first type segments.

An exterior border of a first type segment of the inner circular region contacts the interior border of a second type segment of the outer annular region. An exterior border of a second type segment of the inner circular region contacts the interior border of a first type segment of the outer annular region.

Figure 15:
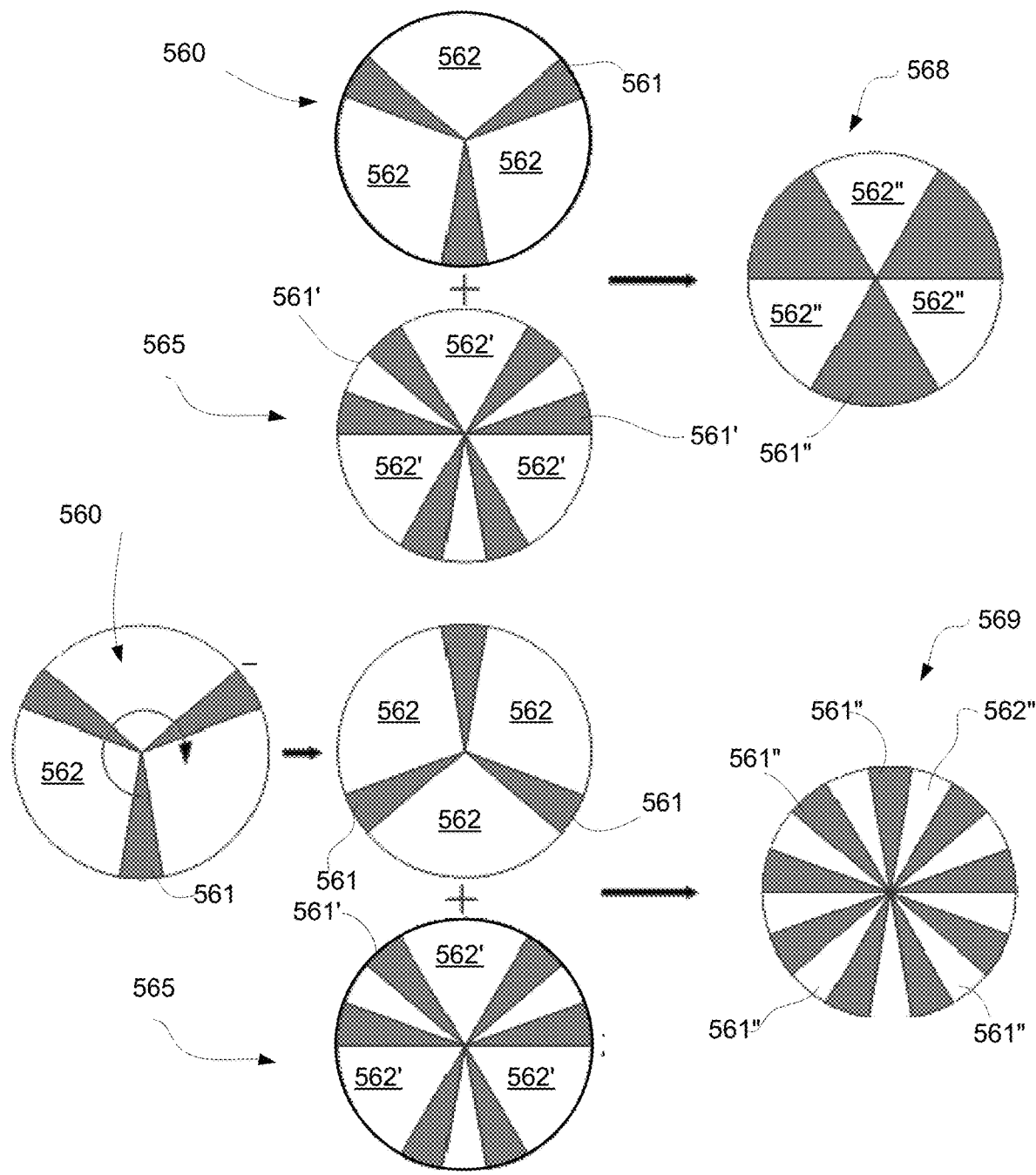
FIG. 15 illustrates at least one example of at least one aperture stop.

FIG. 14 also illustrates aperture stop 540 that include five first type regions 544 that are oblique and five second type segments 546 that are transparent—that are arranged in an interleaving manner. FIG. 15 illustrates a group of aperture stops—the group includes first aperture stop 560 and a second aperture stop 565.

First aperture stop 560 may include three first type segments 561 and three second type segments 562 that are arranged in an interleaved manner and in a radially symmetric manner. The first type segments 561 are thinner (for example by a factor of three) than the second type segments 562.

Second aperture stop 565 may include six first type segments 561' and six second type segments 562' that are arranged in an interleaved manner.

When the first aperture stop 560 and the second aperture stop 565 are aligned they virtually form an aperture stop 568 that includes three first type segments 561" and three second type segments 562" that are radially symmetrical and are interleaved. The width of the first type segments 561" are the same as the width of the second type segments 562". Each first type segment 562" is formed by a continuous of a first type segment 561 of first aperture stop 560 that is surrounded by two first type segments 562 of second aperture stop 565.

When the first aperture stop 560 is rotated (clockwise) by sixty degrees (and the second aperture stop 565 is not rotated) then the first and second aperture stops 560 and 565 virtually form an aperture stop 569 that includes nine first type segments 561" and nine second type segments 562" that are radially symmetrical and are interleaved. The width of the first and second type segments 561" and 562" are the same as the width of the first and second type segments 561' of first aperture stop 560.

It should be noted that the rotation can differ than sixty degrees, the number of the first type segments, the width of the first type segments, the arrangement of the first type segments, the shape of the first type segments, the size of the first type segments, the number of the second type segments, the width of the second type segments, the arrangement of the second type segments, the shape of the second type segments, the size of the second type segments, may differ from those illustrated in FIGS. 13-15.

The system may include aperture stops such as the aperture stops that are listed above. Additionally or alternatively, system may include aperture stops such as those illustrated in US patent application "APERTURE STOP" publication serial number 20160366315 and of US patent application "APERTURE STOP" publications serial number 20170261654, both incorporated herein by reference.

There may be provided a method that may include scanning by a partially blocking bright field unit a semiconductor substrate; checking whether a peeling of an external surface of the semiconductor substrate is found; calculating at least one attribute of the peeling; and determining, based on the calculating, whether to accept the semiconductor substrate, whether to reject the semiconductor substrate, or whether to reject a group of semiconductor substrates that include the semiconductor substrate.

The at least one attribute of the peeling is selected out of at least one of a length, width, area, diameter, and perimeter of the peeling.

Figure 16:
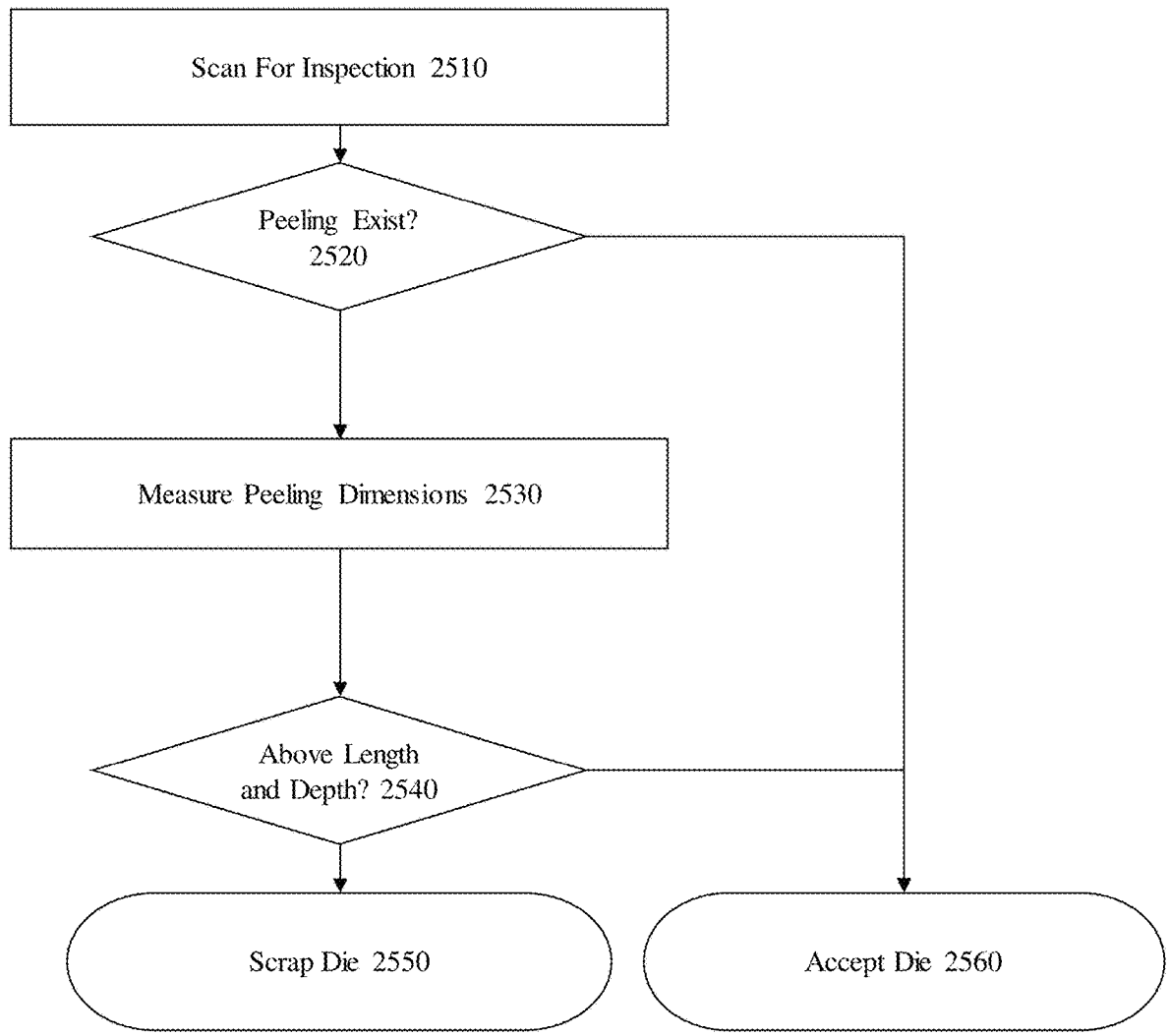
FIG. 16 illustrates an example of a method.

FIG. 16 illustrates method 2500 for evaluating a wafer.

Method 2500 may start by step 2510 of scanning (by a partially blocking bright field unit) a semiconductor substrate.

Step 2510 may be followed by step 2520 of checking if peeling is found.

Step 2520 may be followed by step 2530 of measuring (by the partially blocking bright field unit or by the verification unit) the dimensions of the peeling (length, width, area, diameter, perimeter, etc.).

Step 2530 may be followed by step 2540 of checking the peeling (having the dimensions learnt during step 2540) are acceptable or not—for example checking of the length and depth of the peeling are above a Length threshold and a Depth threshold.

If the answer is negative, then jumping to step 2550 of scrapping the die or even a group of dies that surround the "srapped" die (or deciding to scrap the die).

If the answer is positive, then jumping to step 2560 of accepting the die.

Figure 17:
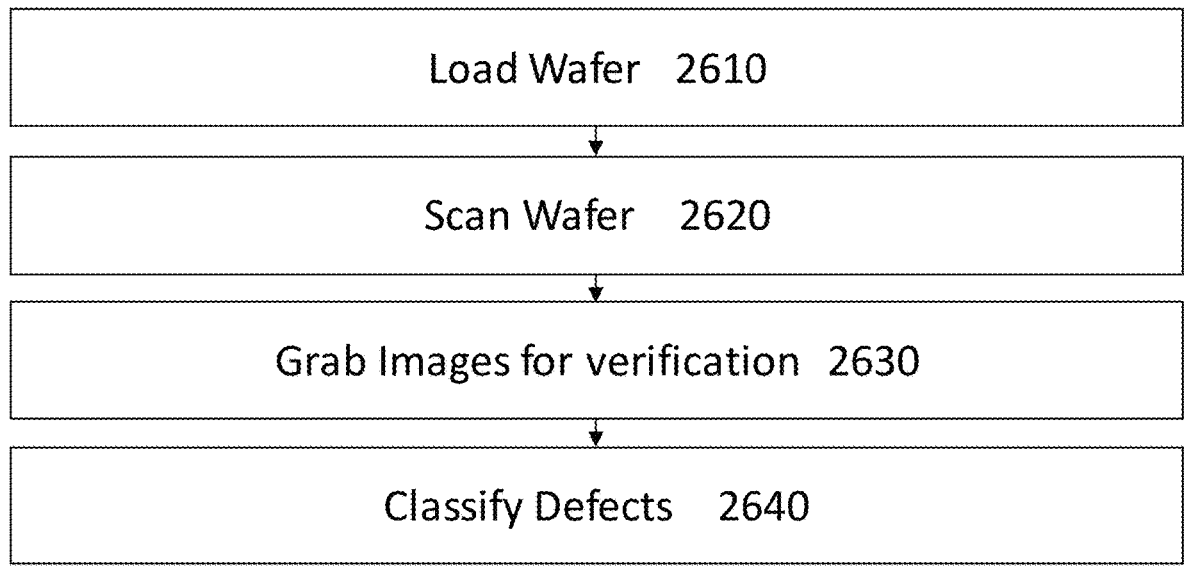
FIG. 17 illustrates an example of a method.

FIG. 17 illustrates method 2600 for evaluating a semiconductor substrate.

Method 2600 may start by step 210 of loading a semiconductor substrate.

Step 2610 may be followed by step 2620 of scanning (by a partially blocking bright field unit) a semiconductor substrate.

Step 2620 may be followed by step 2630 of grabbing images for verification.

Step 2630 may be followed by step 2640 of classifying defects.

It should be noted that any of the mentioned above systems may be used for various purposes and may execute various methods that differ from crack detection. There may be provided various methods that differ from method 2500.

FIG. 18 illustrates method 2700 for detecting pillar defects in epitaxial growth over substrate.

Pillar defects are epitaxial growth defects where above the flat surface a pillar (column) grows instead of a flat surface. In the vicinity of the pillar the surface inclination deviates from the horizontal one thus making it able to detection by the partially blocking bright field unit.

After the step 2720 a step 2730 performs disqualification or verification by a verification channel or performs metrology calculations: length, width, area, perimeter, diameter, etc. of the inclination areas above the planar of the substrate.

Method 2700 may start by step 2710 of scanning a semiconductor substrate that have an upper layer that was manufactured by an epitaxial growth process. The scanning is performed by the partially blocking bright field unit. The outcome of step 2710 is one or more images of one or more regions of the semiconductor substrate.

The pillar defects are much smaller than the surfaces that are inclined due to the existence of the pillar defects—and thus their presence may be detected (in an indirect manner) using optics of lower resolution that is required for imaging the pillars. This reduces the cost of the optics and/or increases the throughput—by using wider beams.

Step 2710 may be followed by step 2720 of processing the one or more images to find locations that should have been flat—but are inclined. Locations that should have been flat may be determined using design information (such as CAD data) actual measurements of similar locations—using for example cell to cell, die to die, die to design comparison methods, and the like.

Profiles of inclined surfaces that are formed due the pillar defects may be learnt using machine learning, by scanning reference semiconductor substrates that include such defects, and the like.

Step 2720 may include searching for bright spots (indicating facets with off horizontal inclination) that that are above a grey level=X (predefined value) and from a cluster of size>Y (predefined value) pixels can be marked as suspect defects.

There may be provided a method for inclinations (even minor) of surfaces, for measuring surface roughness using the partially blocking bright field unit. These methods may include haze inspection.

There may be provided an inspection unit that may include a phase shifting bright field unit that may change the phase of light beams. The phase shifting bright field unit may include different regions that introduce phase shifts and different regions that do not introduce phase shift—or otherwise perform phase shifting to light beams that propagate at some locations within the aperture stop and not perform phase shifting of light beams that propagate at other locations within the aperture stop. It should be noted that the aperture stop may perform different phase shifts at different regions of the aperture stop.

The phase shifting bright field unit may be provided in addition to the non-blocking bright field unit, instead of the non-blocking bright field unit, in addition to the partially blocking bright field unit, or instead of the partially blocking bright field unit.

An SLM may provide the functionality of the phase shifting bright field unit and/or the non-blocking bright field unit and/or the non-blocking bright field unit.

There may be any spatial relationship between the phase shifting bright field unit, the non-blocking bright field unit and the partially blocking bright field unit.

The phase shifting bright field unit may include a phase shifting objective lens that may be replaced wither other objective lenses.

Figure 19:
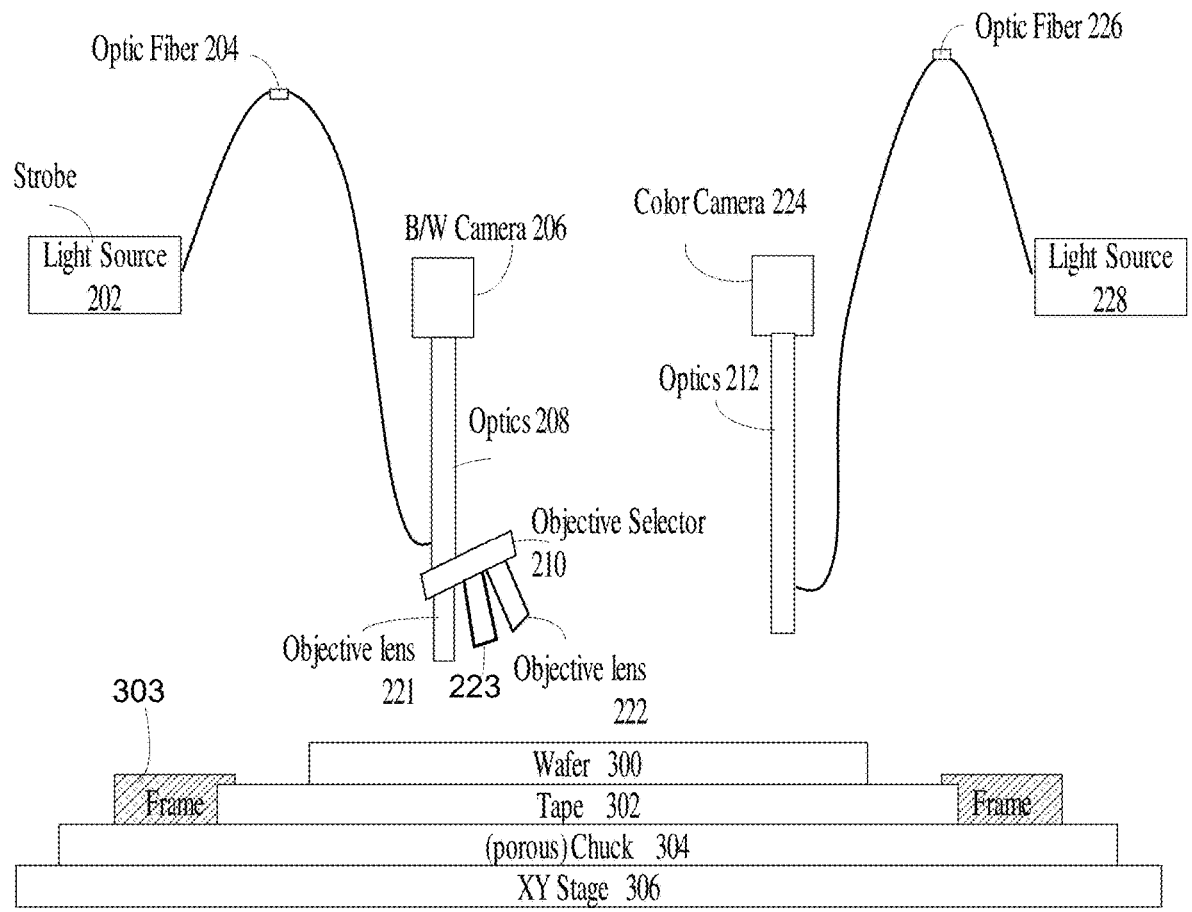
FIG. 19 illustrates an example of a semiconductor substrate and a system.

FIG. 19 illustrates a system 202'. System 202' differs from system 200 of FIG. 5 by including third objective lens 223 in addition to first objective lens 221 and second objective lens 222.

Third objective lens 223 belongs to a phase shifting bright field unit (and may be referred to as a phase shifting objective lens. The phase shifting bright field unit may include an objective lens and a phase shifting element—that mat be located in an exit pupil.

The phase shifting element may have any shape—depending on the required phase shift—and may have the same shape as any of the aperture stops mentioned above.

There may be provided any combination of objective lenses 221, 222 and 223. The third objective lens 223 may be another magnification non-blocking bright field unit.

The third objective lens 223 may also be included in system 21 of FIG. 6.

In a process of semiconductor substrate bonding, voids and foreign particles may be located at the interface between one semiconductor substrate (for example—carrier wafer) and the other.

These voids and foreign particles are internal defects that are hard to detect directly.

It has been found that these voided can be indirectly detected by using the partially blocking bright field unit—by searching for inclinations of the external surface (at locations that should have been flat) of the bonded semiconductor substrates.

Figure 20:
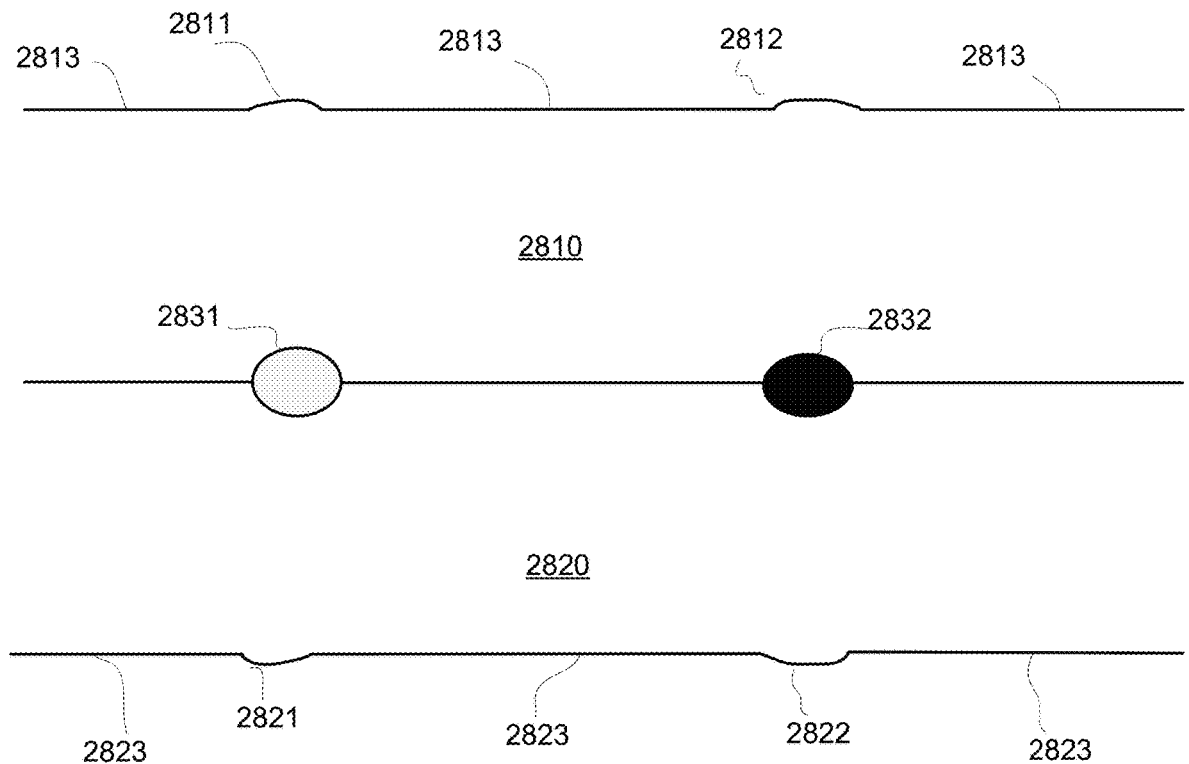
FIG. 20 illustrates a pair of semiconductor substrates that are bonded to each other.

FIG. 20 illustrates first semiconductor substrate 2810, second semiconductor substrate 2820 that are bonded to each other. Void 2831 and foreign particle 2832 are formed in the interface between the semiconductor substrates. These defects cause slight deformations 2811 and 2812 to be formed on the otherwise flat upper surface 2813 of first semiconductor substrate 2810 and cause slight deformations 2821 and 2822 to be formed on the otherwise flat lower surface 2823 of second semiconductor substrate 2820.

Standard imaging is not capable (neither BF and neither DF) to detect slight deformations.

These slight deformations may be detected using the suggested system and method 2800.

Method 2800 may start by step 2870 of scanning the external surface of one or more bonded semiconductor substrates. The scanning is performed by the partially blocking bright field unit. The outcome of step 2870 is one or more images of one or more regions of the external surfaces of the one or more bonded semiconductor substrates.

Step 2870 may be followed by step 2890 of processing the one or more images to find locations that should have been flat—but are inclined. These locations may be indicative of the internal defects—formed in the interface between bonded semiconductor substrates. Locations that should have been flat may be determined using design information, actual measurements of similar locations—using for example cell to cell, die to die, die to design comparison methods, and the like.

Profiles of slight deformations that are formed due such inner defects of bonded semiconductor substrates may be learnt using machine learning, by scanning bonded semiconductor substrates that include such defects, and the like. During the learning period bonded semiconductor substrates that have slight deformation may be detected or undergo any other intrusive root failure analysis to find a match between the slight deformations and inner defects.

Step 2890 may include searching for bright spots (indicating facets with off horizontal inclination) that that are above a grey level=X (predefined value) and from a cluster of size>Y (predefined value) pixels can be marked as suspect defects.

Step 2890 may be followed by performing intrusive failure analysis steps.

Different Semiconductors substrates may be connected to each other by bumps. Accordingly—an internal array of bumps may be located between two semiconductors substrates. This internal array of bumps may not be seen from outsides these semiconductors substrates.

Bump defects such as missing bumps, bump misalignment (bump locates at a different location that the intended location), bad bump connections and other defects cannot be seen when viewing the semiconductors substrates from above (or from the bottom).

The bumps may form a minor deviations of the external surfaces of the semiconductors substrates. A non-faulty bump may form a certain minor deviation (for example a certain concave area) while faulty bumps may case other minor deviations.

The minor deviations may be detected by using the partially blocking bright field unit—by searching for the minor deviations or the lack of such minor deviations (when a bump is missing).

Figure 22:
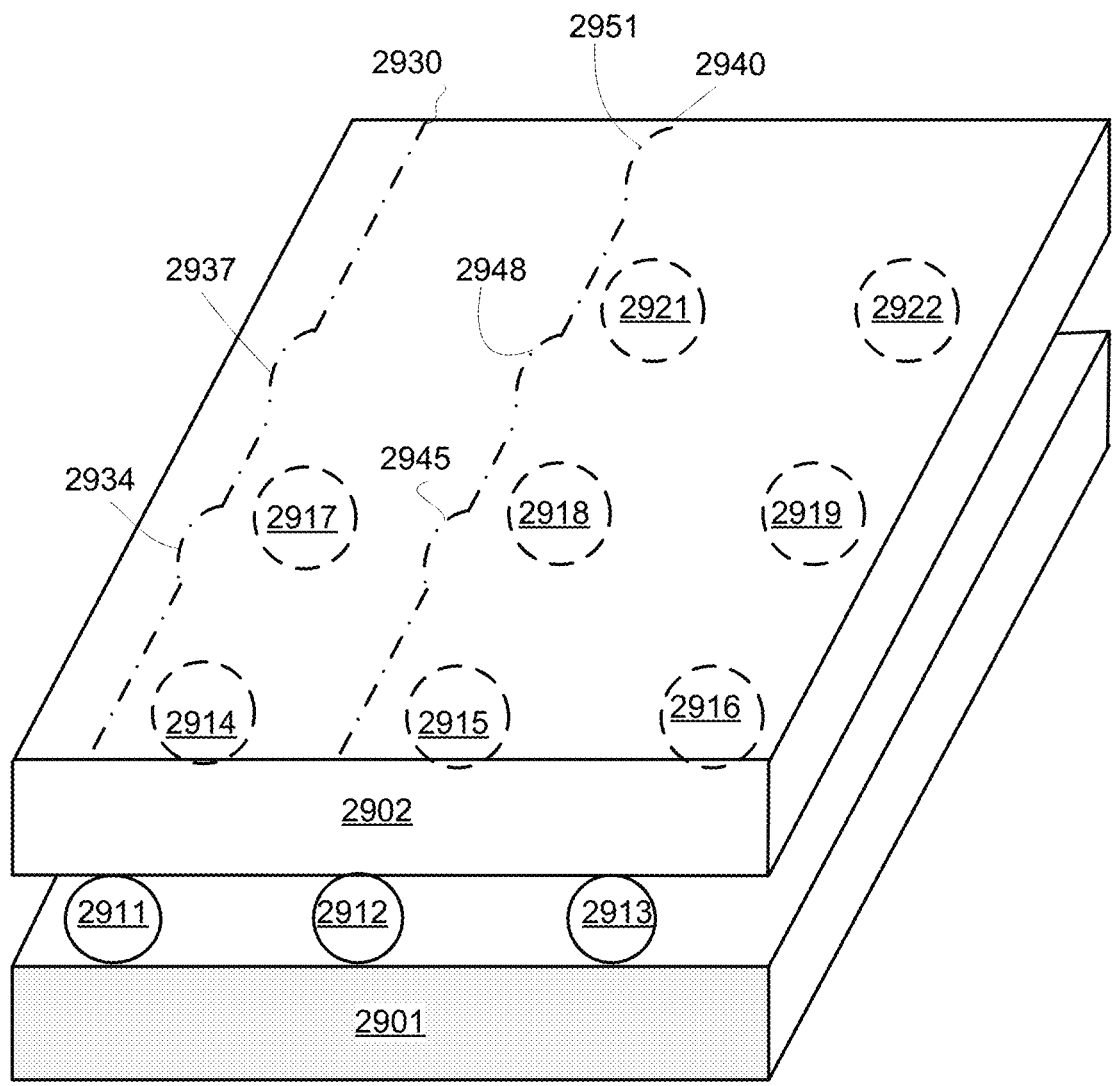
FIG. 22 illustrates an array of bumps and a pair of semiconductor substrates.

FIG. 22 illustrates first die 2901, second die 2902, and an internal array of bumps (including bumps 2911, 2912, 2913, 2914, 2915, 2916, 2917, 2918, 2919, 2921 and 2922) positioned between these dies.

The internal array of bumps should have included twelve bumps—but one bump (upper left bump) is missing. The missing bump can be detected by the absence of minor deviation about the expected location of the bump.

FIG. 22 illustrates the distribution of height along two imaginary lines 2930 and 2940.

Imaginary line 2930 passes over bump 2914 (see minor deviation 2934), above bump 2917 (see minor deviation 2937) and above the location of the missing bump (no minor deviation). The height is substantially constant between the minor deviations.

Imaginary line 2940 passes over bump 2915 (see minor deviation 2935), above bump 2918 (see minor deviation 2938) and above bump 2921 (see minor deviation 2951). The height is substantially constant between the minor deviations.

FIG. 23 illustrates method 3000.

Method 3000 may start by step 3010 of scanning the external surface of a semiconductor substrate to provide one or more images of one or more regions of the external surface of the semiconductor substrate. One or more internal bumps are located between the semiconductor substrate and another semiconductor substrate. The scanning is performed by the partially blocking bright field unit.

Step 3010 may be followed by step 3020 of processing the one or more images to find bump defects—such as missing bumps, bad bump connections, bump misalignments, and the like.

Locations that should include minor deviation that are indicative of non-faulty bumps can be found in design data (such as CAD data), can be estimated based on previous inspections, and the like. Step 3010 may include searching for bright spots (indicating facets with off horizontal inclination) that that are above a grey level=X (predefined value) and from a cluster of size>Y (predefined value) pixels can be marked as suspect defects. The CAD data may be used in order to detect in the image achieved by the partially blocking bright field unit—to identify and detect missing bumps, misalignment of the inner layer bumps, etc.

Profiles of non-faulty bumps as well as one or more bump defects may be learnt using machine learning, by scanning semiconductors substrates that are connected to bumps, and the like. During the learning period, semiconductors substrates that are connected to faulty bumps may be dissected or undergo any other intrusive root failure analysis to find a match between the minor deviation and bump defects.

Step 3020 may be followed by performing intrusive failure analysis steps. After the step 3020 a step 3030 performs disqualification or verification by a verification channel or performs metrology calculations: length, width, area, perimeter, diameter, etc. of the inclination areas above the planar of the substrate.

FIG. 24 illustrates method 3100.

Method 3100 may include operating any of the systems illustrated above.

Method 3100 may start by step 3110 of performing a first inspecting session that comprises inspecting a first region of a semiconductor substrate, wherein the inspecting of the first region comprises blocking, by a partially blocking bright field unit, any specular reflection that fulfills the following: (a) the specular reflection is caused by illuminating, along a first axis, of an area of the wafer, (b) the specular reflection propagates along a second axis, (c) the first axis and the second axis are symmetrical about a normal to the area of the wafer, and (d) the normal is parallel to an optical axis of the partially blocking bright field unit.

Method 3100 may also include step 3120 of performing a second inspecting session that comprises inspecting a second region of the semiconductor substrate, wherein the inspecting of the second region comprises passing to an image plane any specular reflection that fulfills the following: (a) the specular reflection is caused by illuminating, along the first axis, of an area of the wafer, (b) the specular reflection propagates along the second axis, (c) the first axis and the second axis are symmetrical about the normal, and (d) the normal is parallel to the optical axis of the partially blocking bright field unit.

The first and second regions may be the same region—which is inspected using different settings of the inspection systems. Step 3120 may be applied on locations detected as suspected (or of interest) during step 3110—but this is not necessarily so.

Step 3110 and/or step 3120 may include obtaining images.

Method 3100 may include step 3130 of processing, by a processor, images acquired during at least one step of steps 3110 and 3120.

The processing may include finding suspected defects, finding defects, verifying suspected defects, metrology, and the like.

There may be provided an inspection system that may include an inspection unit that comprises a partially blocking bright field unit and a verification unit; wherein the partially blocking bright field unit is configured to block any specular reflection that fulfills the following: (a) the specular reflection is caused by illuminating, along a first axis, of an area of the wafer, (b) the specular reflection propagates along a second axis, (c) the first axis and the second axis are symmetrical about a normal to the area of the wafer, and (d) the normal is parallel to an optical axis of the partially blocking bright field unit.

The verification unit may include a non-blocking illumination unit, and a color camera configured to provide a color image of the semiconductor substrate.

The partially blocking bright field unit may be configured to acquire images, and wherein the inspection system further comprises a processor that is configured to process the images and to detect suspected defects at locations that correspond to locations of areas of the semiconductor substrate that have an inclination that deviates from an expected inclination.

The verification unit may be configured to review the suspected defects.

Figure 25:
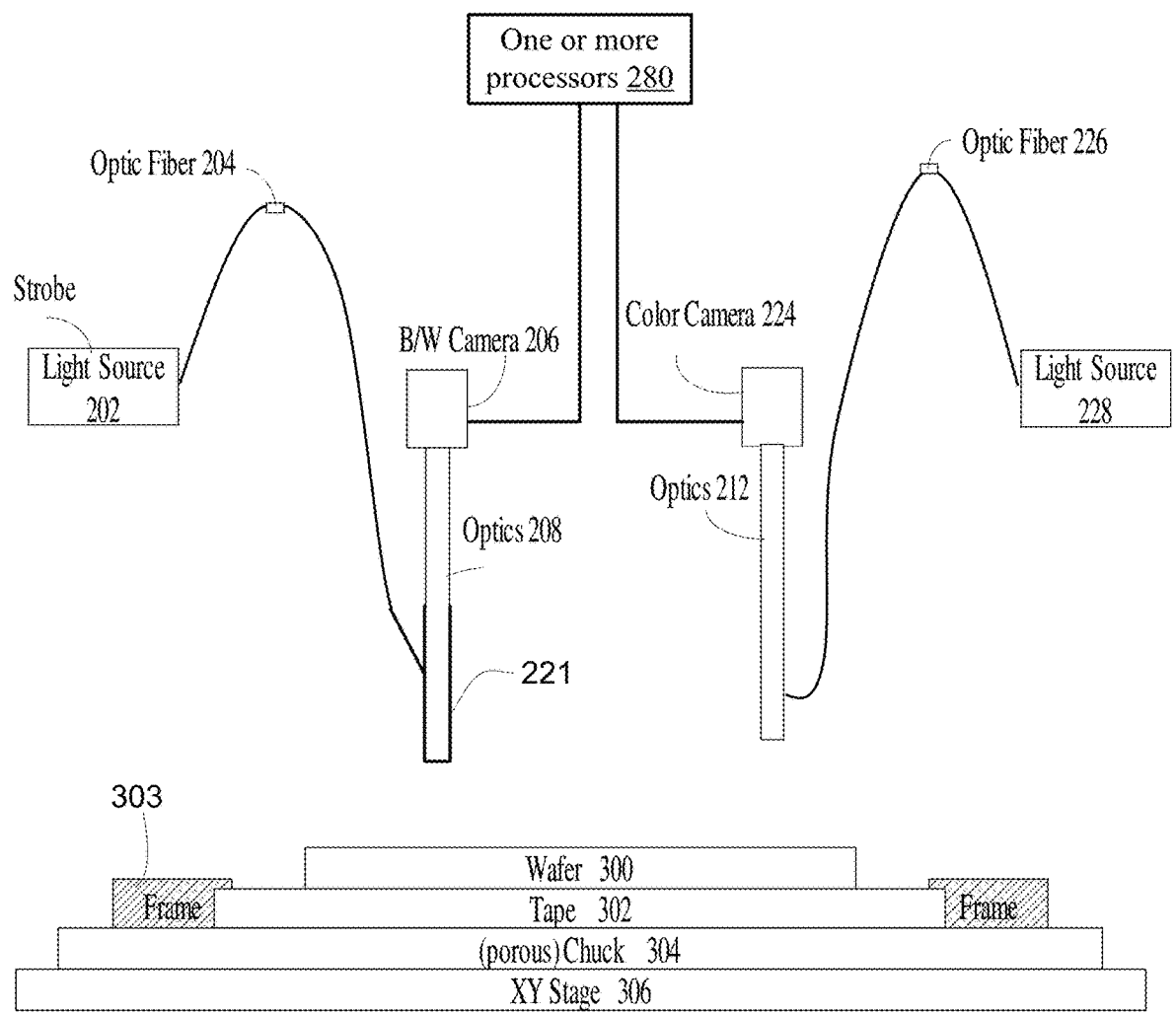
FIG. 25 illustrates an example of a semiconductor substrate and a system.

FIG. 25 illustrates system 204' for inspecting a semiconductor substrate. System 204' differs from system 200 of FIG. 5 by not including the non-blocking bright field unit.

There may be provided metrology (using the partially blocking bright field unit), verifications, etc. The system may generate metrological information of the inclined surface, in particular width, length and area. The data may be generated by using the combination of the blocked and non-blocked channels or only the non-blocked.

Figure 26:
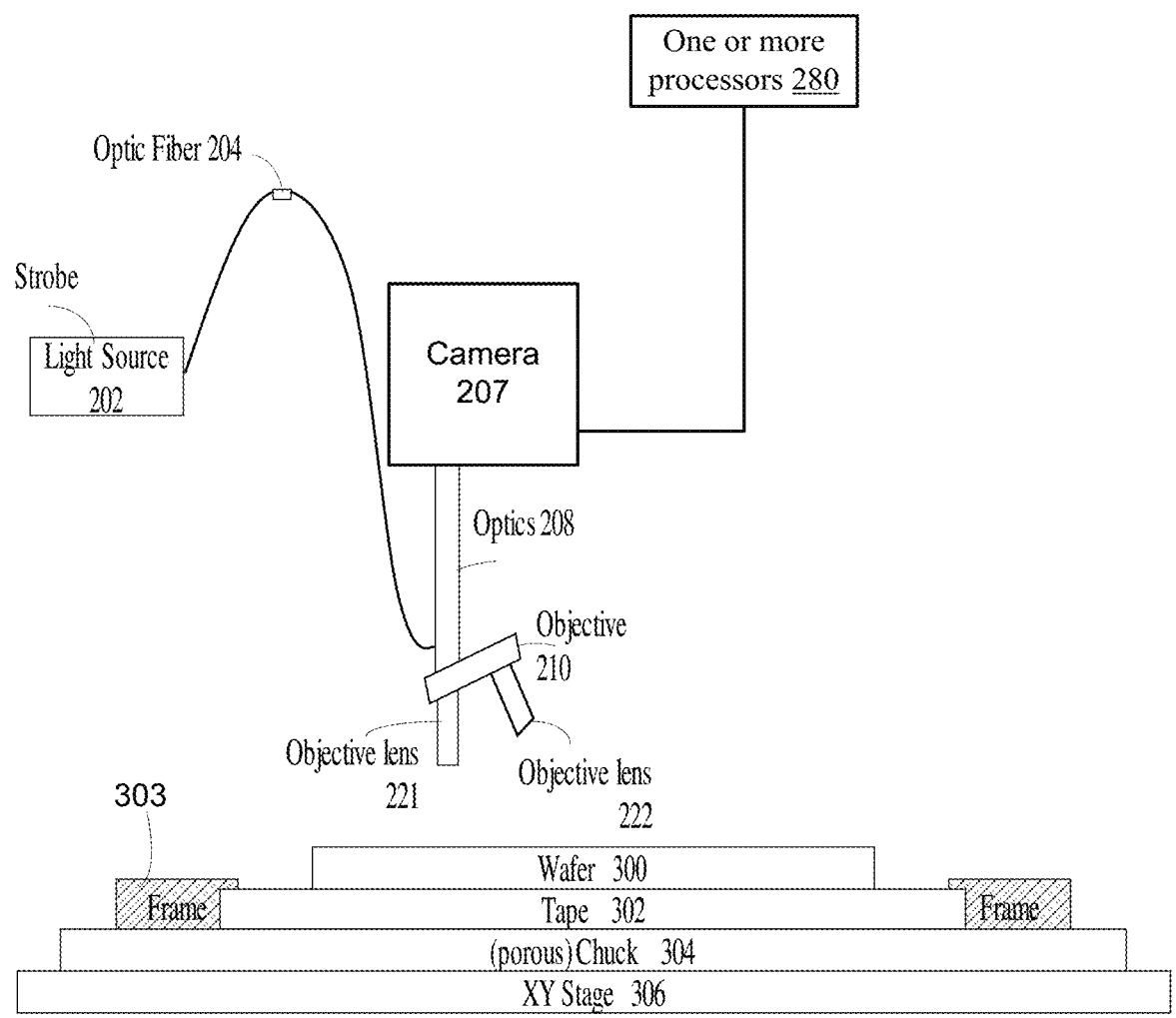
FIG. 26 illustrates an example of a semiconductor substrate and a system.

FIG. 26 illustrates a system.

The system of FIG. 26 differs from system 21 of FIG. 6 by including a camera 207 that may be a black and white camera and/or a color camera.

Figure 27:
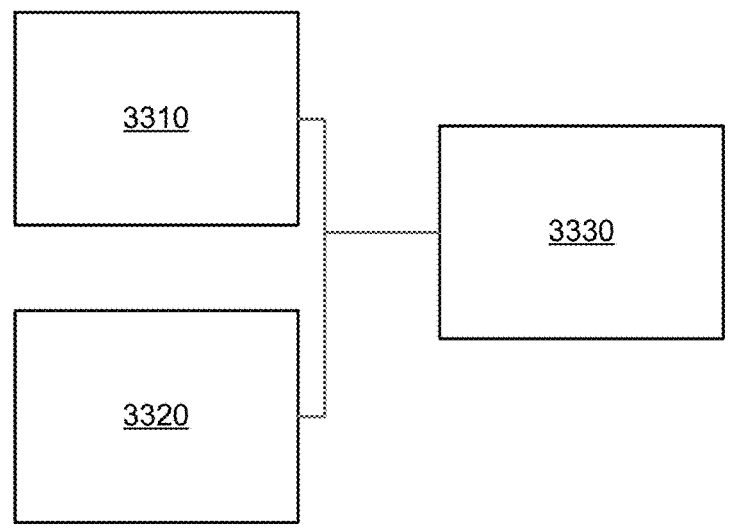
FIG. 27 illustrates an example of a method.

FIG. 27 illustrates method 3300.

Method 3300 starts by step 3310 of operating an inspection unit in a first mode, wherein the inspection unit comprise an exit pupil, an illumination module and an image sensor; wherein the operating in the first mode comprise illuminating an entirety of the exit pupil, and receiving by the image sensor light from the entirety of the exit pupil. During this step one or more images of one or more area of one or more semiconductor substrates are acquired.

Method 3300 may include step 3320 of operating the inspection unit in a second mode, wherein the operating in the second mode comprises positioning an aperture stop in the exit pupil thereby preventing the illumination module from illuminating the entirety of the exit pupil, and prevents, by blocking at least one specular reflectance, the image sensor from receiving light from the entirety of the exit pupil.

During this step one or more images of one or more area of one or more semiconductor substrates are acquired.

The first and second modes may be sued for acquiring images of the same semiconductor substrates or of other semiconductor substrates.

The first and second modes may be used in association with a same type of defects (bump defects, cracks or any other types of defects). Alternatively, the first mode may be used to file one type of defect and the second mode may be used to find another type of defects.

Either one of the first and second modes may be used to perform metrology.

Step 3320 may include having an aperture stop is configured to block any specular reflection that fulfills the following: (a) the specular reflection is caused by illuminating, along a first axis, of an area of the wafer, (b) the specular reflection propagates along a second axis, (c) the first axis and the second axis are symmetrical about a normal to the area of the wafer, and (d) the normal is parallel to an optical axis of the partially blocking bright field unit; and the non-blocking bright field unit is configured to pass to the image plane any specular reflection that fulfills the following: (a) the specular reflection is caused by illuminating, along the first axis, of an area of the wafer, (b) the specular reflection propagates along the second axis, (c) the first axis and the second axis are symmetrical about the normal, and (d) the normal is parallel to the optical axis of the partially blocking bright field unit.

Method 3300 may include step 3330 of processing, by a processor, images acquired during at least one of the first mode and the second mode.

The processing may include finding suspected defects, finding defects, verifying suspected defects, metrology, and the like.

FIGS. 28-36 illustrate various example of aperture stops that can be used in system 200 and/or system 201 and/or any other method illustrated in the specification.

Figure 28:
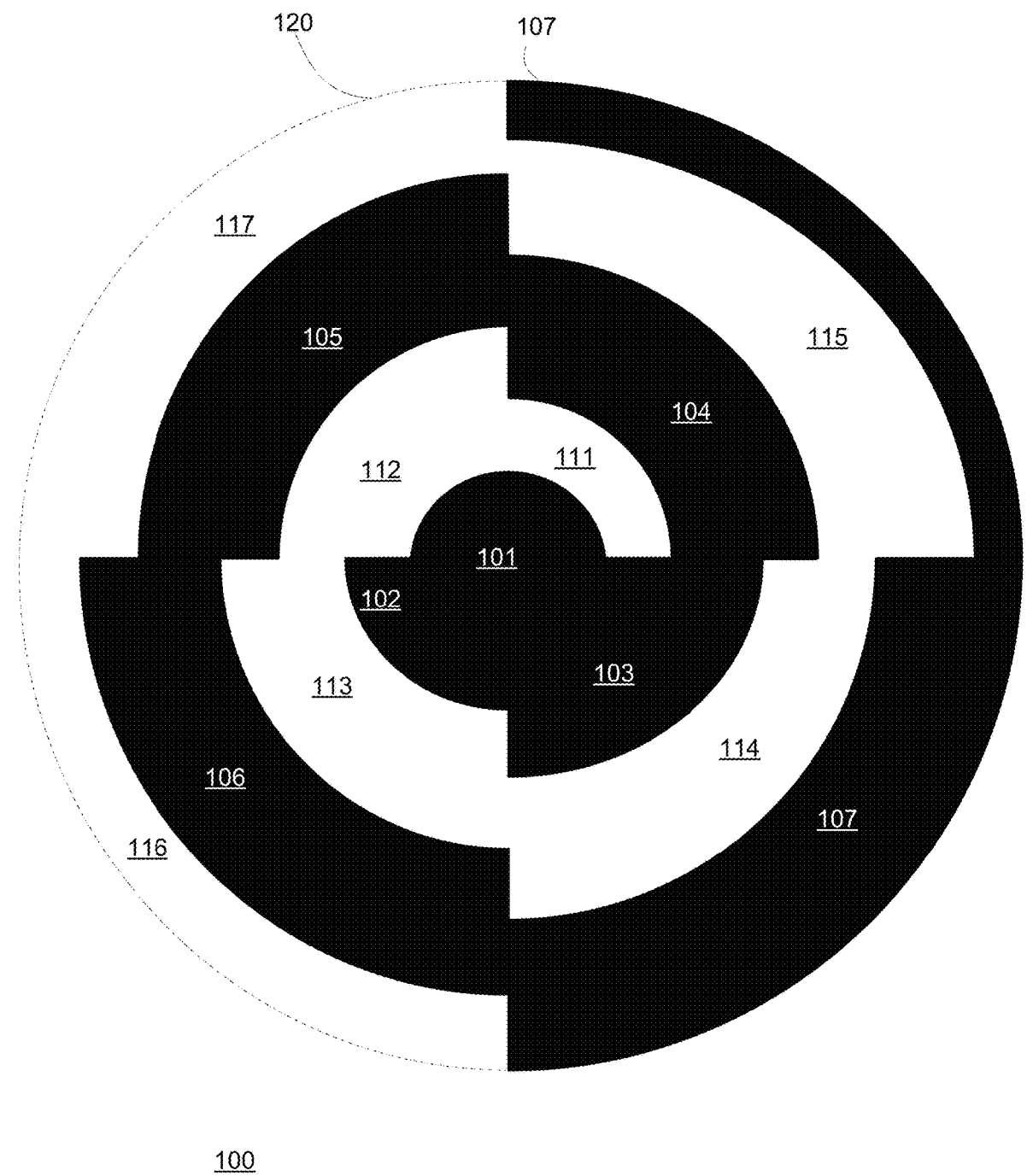
FIG. 28 illustrates at least one example of at least one aperture stop.

FIG. 28 illustrates an aperture stop 100 according to an embodiment of the invention. Within a circular region 120 there are opaque areas 101-107 and openings 111-117.

Figure 29:
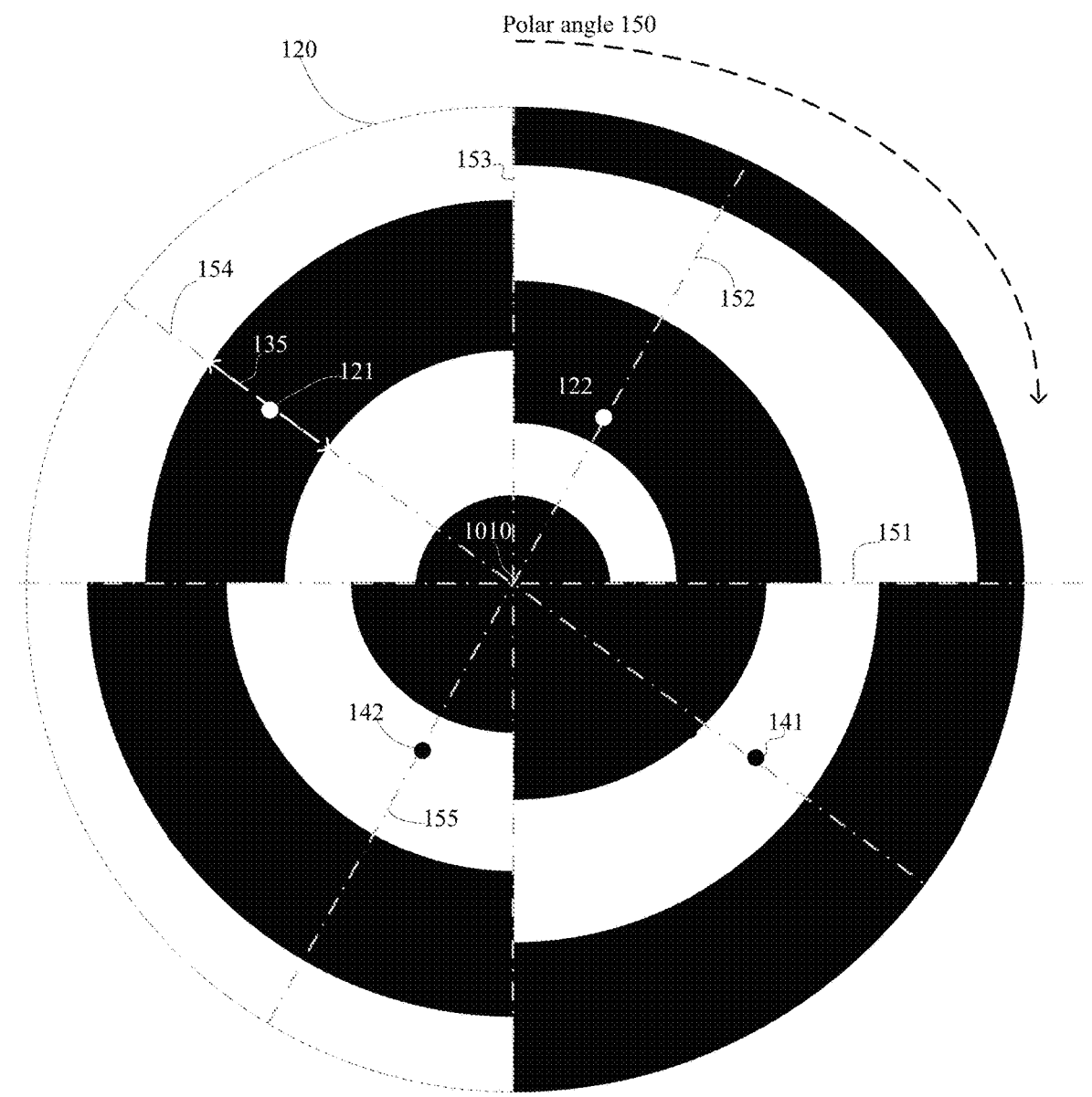
FIG. 29 illustrates at least one example of at least one aperture stop.

The bright regions are the material and the black voids are the openings. The structure of the openings is such that, when viewed at a radial cross section, there are alternating areas of material and openings. In addition, at any given angle, points of equal distance (i.e. the same radius) from the center of the aperture stop are made of opposite materials (one belongs to an opening and the other belongs to an opaque area). It should be noted that, there are some advantages to retain a low specular reflection for improving the process of building the wafer map. This allows a full wafer scan and requires die to die alignment, etc., which can improve with a low specular reflection FIG. 29 illustrates that for each point of incidence (141 and 142) within an opening there is a corresponding point of specular reflectance (121 and 122) that is blocked by an opaque area. The corresponding point and the point of incidence "belong" to the same virtual diameter (152 and 154). This is true for all polar angles (for any diameter of any orientation—such as but not limited to virtual diameters 151, 152, 153 and 154)). Outside opaque area 101 there is a symmetry between opaque points and opening points.

FIG. 29 also illustrates that each opaque area is narrow from a radial point of view—if spans along a limited angular range. This enables reflected rays from surface with a small tilt (in relation the horizon) to pass through the aperture stop 100. Typical values had a peak response at 0.5 degree, and a meaningful response between 0.3 degrees to 1 degree, with a very low specular response at 0 degrees.

The outer diameter of the aperture stop should match the diameter of the objective lens. The center of the aperture can be either open or full.

Figure 30:
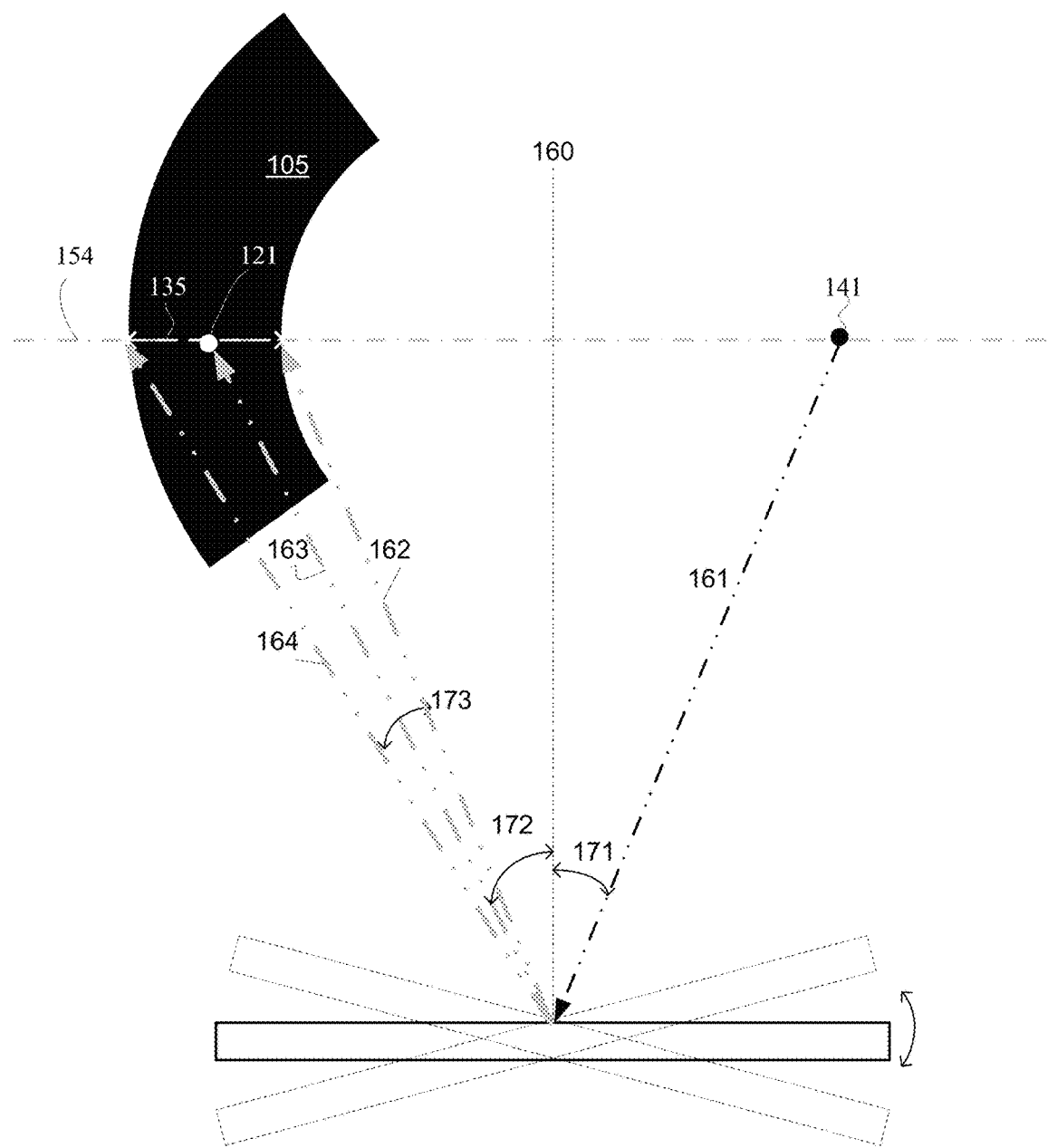
FIG. 30 illustrates at least one example of at least one aperture stop.

FIG. 30 illustrates a mapping between opening point 141, a corresponding opaque 121, and angles of reflection that slightly deviate from the specular reflection angle, according to an embodiment of the invention.

Ray 161 impinges through point of incidence 141 and has an angle of incidence 171. When the illuminated object (illuminated point of the object) is horizontal the reflected ray 163 is reflected at an angle of reflection 172 that equals angle of incidence 171. Reflected ray 163 is blocked by opaque area 105. The width 135 of opaque area 105 is tailored in order to block reflected rays that are confided to a small angular deviation 173 from angle of reflection 172. Reflected rays 162 and 164 (reflected from tilted areas of the wafer—illustrated by tilted boxes) are not blocked by opaque area 105 and pass near the borders of opaque area 105.

Figure 31:
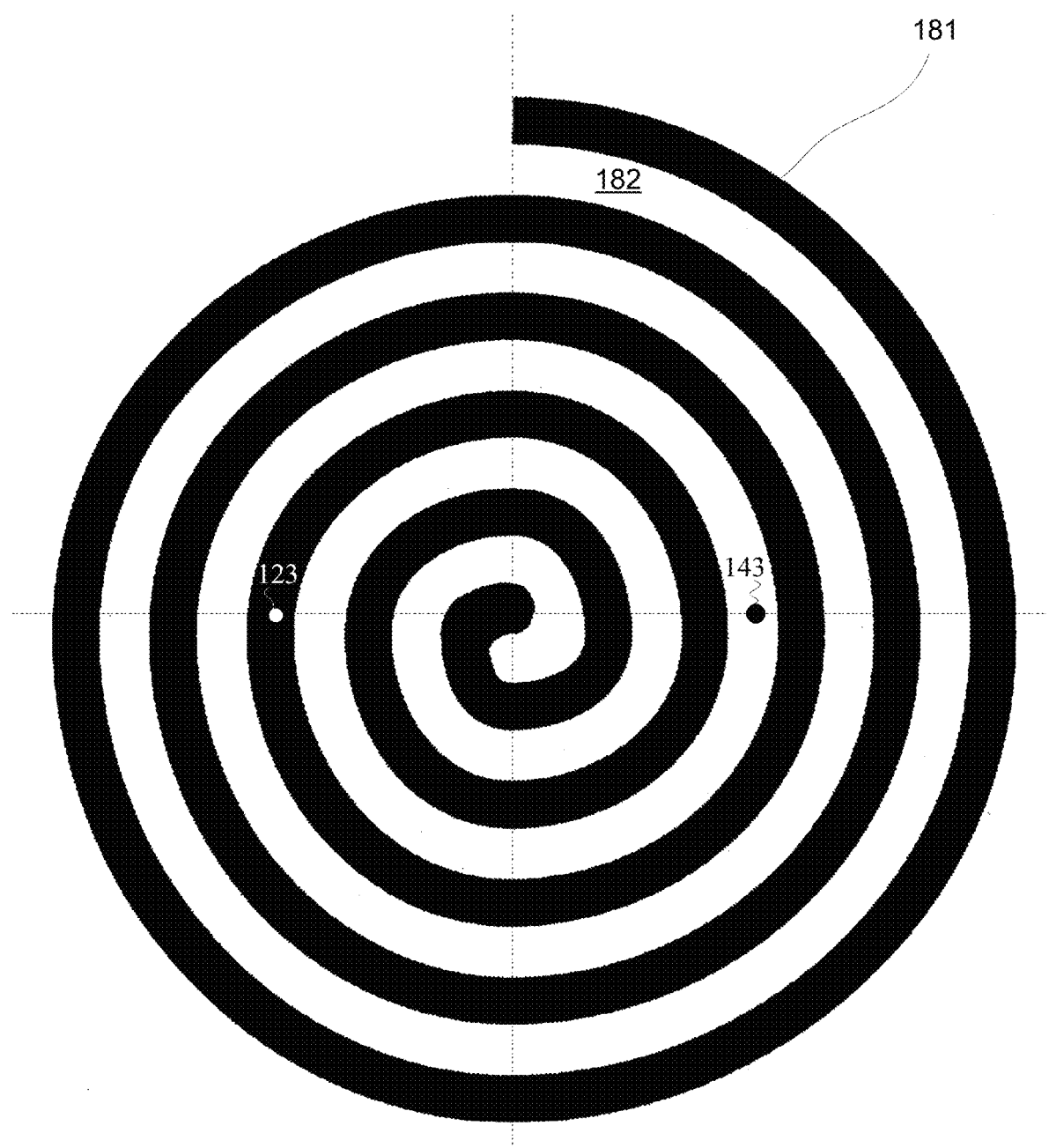
FIG. 31 illustrates at least one example of at least one aperture stop.

FIG. 31 illustrates an aperture stop 100 according to an embodiment of the invention.

Aperture stop 100 includes opaque spiral area 181 that is surrounded by one or more opening areas 182. Each opening point (such as 143) is mapped to an angle of illumination and is associated with a corresponding opaque region point (such as point 123) of the opaque spiral area that is mapped to an angle of specular reflectance from the angle of illumination mapped to the opening point. The width of the opaque spiral area 181 may be tailored such as not to block reflections that are not specular reflections and deviate from the specular reflection by few degrees.

FIG. 32 illustrates an aperture stop 410 that include a non-circular region that is shaped as a square 420 that include a triangle shaped opening 424 and a trapezoid shaped opening 422 that are surrounded by opaque region 412.

Square 420 has a symmetry axis 428 (oriented in −45 degrees) and an asymmetry axis 428 that is oriented in 45 degrees.

Asymmetry axis 428 is referred to as an asymmetry axis because within square 420 each opening point that is located at one side of the asymmetry axis has a corresponding opaque point that is located at a mirror location—at the other side of the asymmetry axis.

Triangle shaped opening 424 is "mirrored" by a triangle shaped opaque region 421. Trapezoid shaped opening 422 is "mirrored" by a trapezoid shaped opaque region 423.

Figure 33:
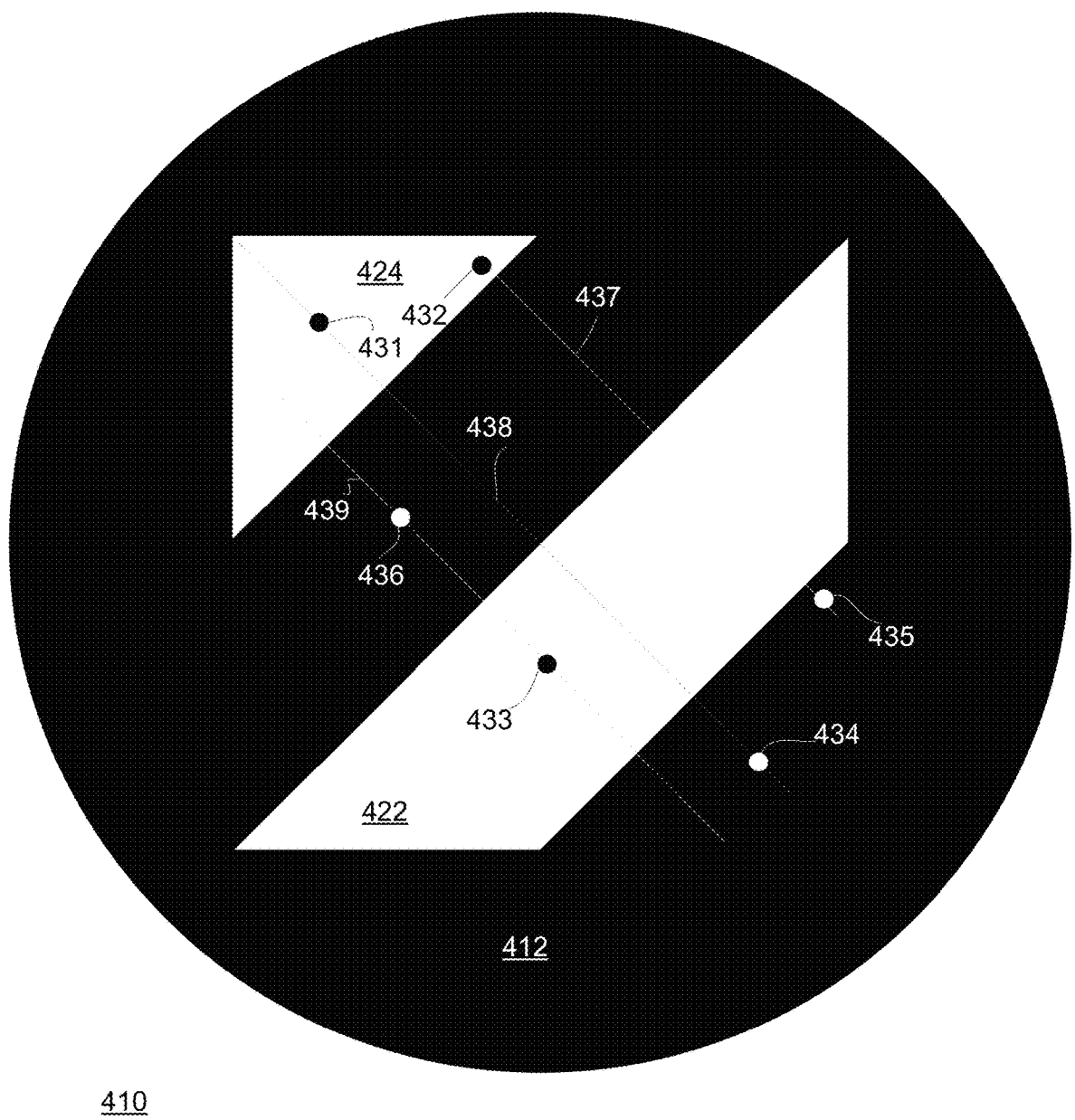
FIG. 33 illustrates at least one example of at least one aperture stop.

FIG. 33 illustrates three opening points 431, 432 and 433 and their corresponding opaque points 434, 435 and 436 respectively.

Points 431 and 434 are positioned on axis 428, points 432 and 435 are positioned on axis 427, and points 433 and 436 are positioned on axis 426. Axes 436, 437 and 438 are parallel to axis of symmetry 429.

It should be noted that the axis of asymmetry and axis of asymmetry can be oriented in other manners (for example— not oriented in 45 degrees and/or −45 degrees). The orientation may be set according to the expected or actual orientation of the detects of interest.

For example—aperture stop 410 was designed to inspect defects that are expected to be oriented along the X-axis and/or the Y-axis (corresponding to orientation of zero and ninety degrees).

The shape and orientation of the triangle shaped opening 424 and a trapezoid shaped opening 422 allow to receive non-specular reflections from defects that are horizontal or vertical.

Figure 34:
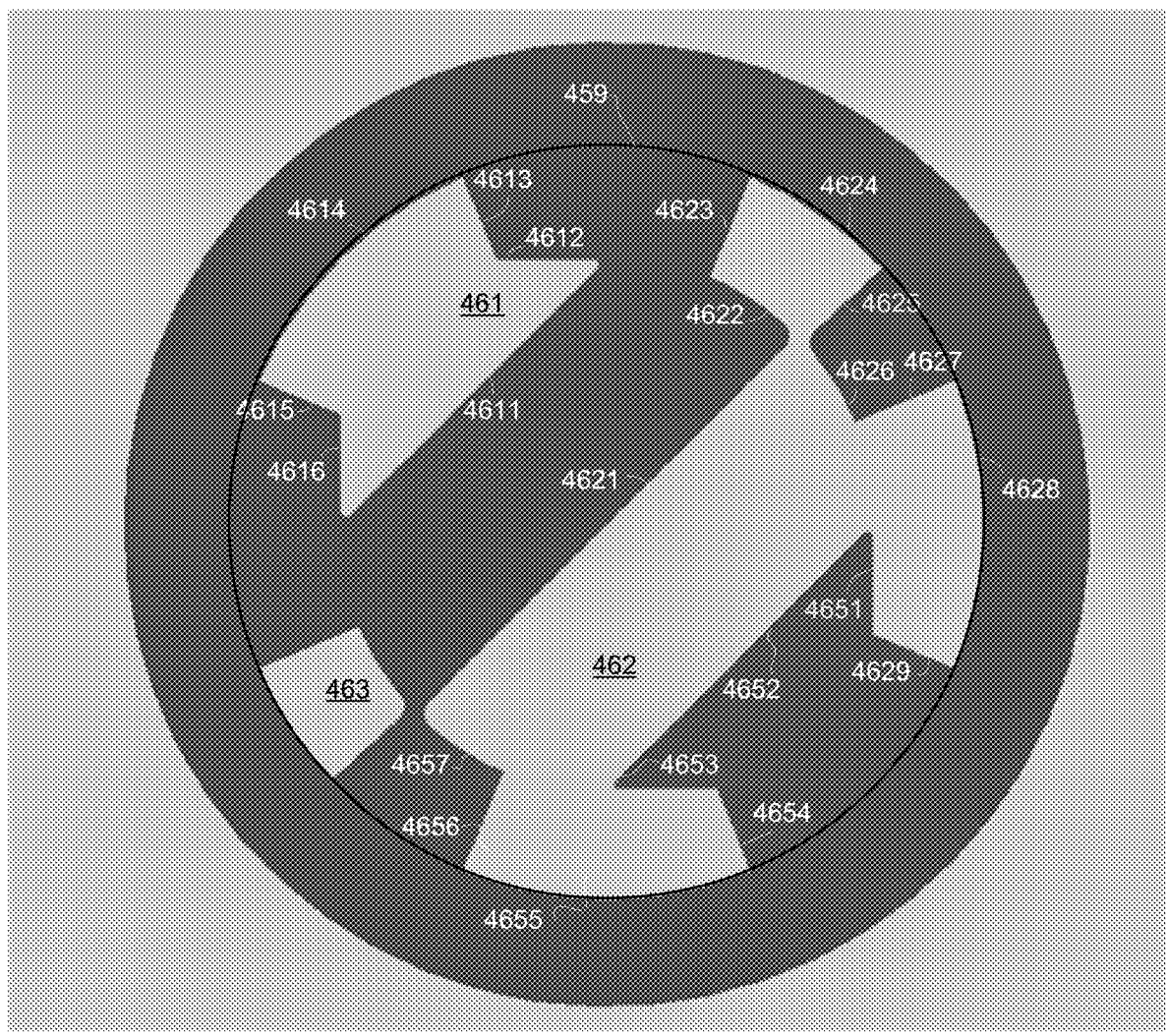
FIG. 34 illustrates at least one example of at least one aperture stop.
Figure 35:
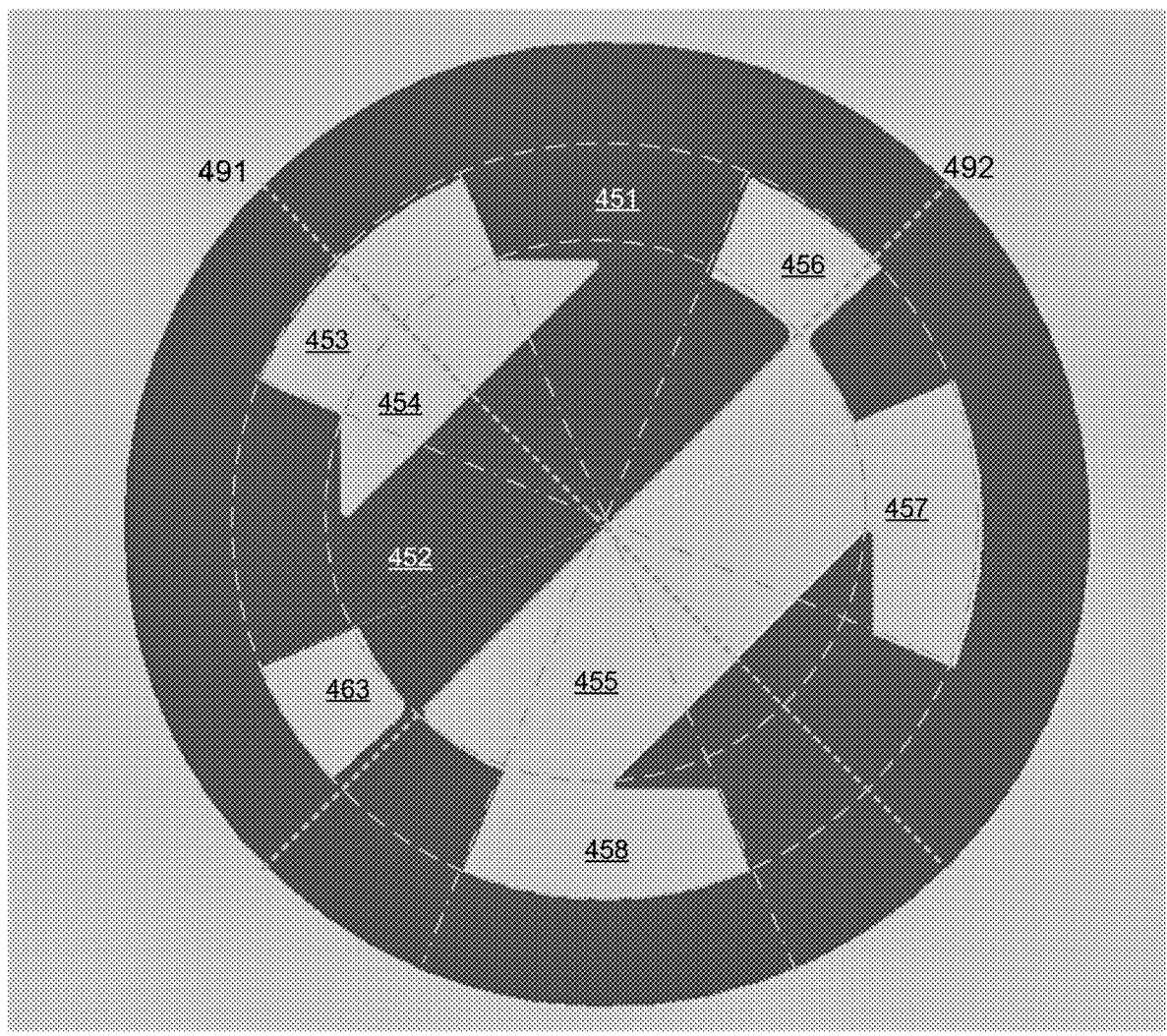
FIG. 35 illustrates at least one example of at least one aperture stop.
Figure 36:
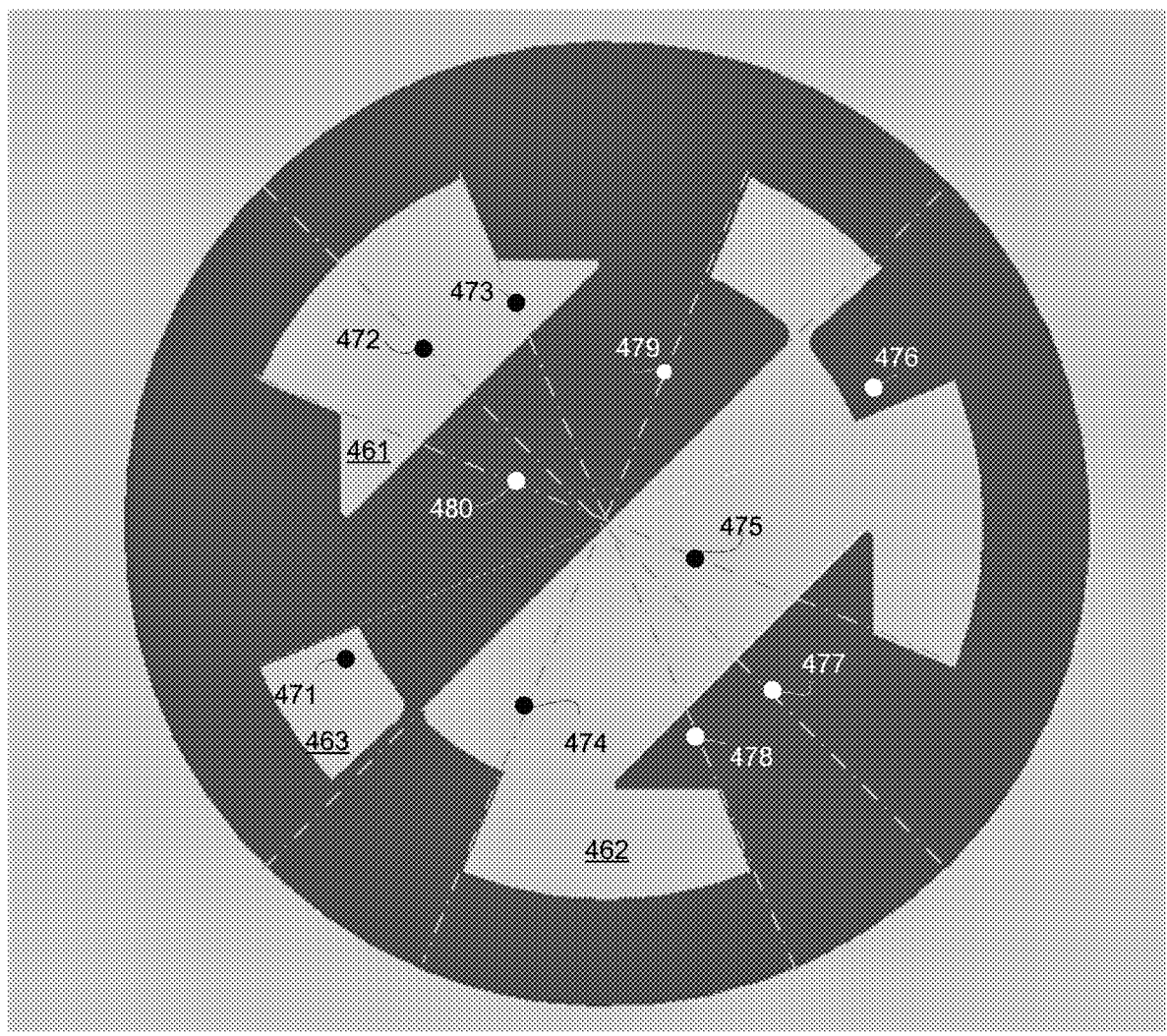
FIG. 36 illustrates at least one example of at least one aperture stop.

FIGS. 34-36 illustrate an aperture stop 450 according to an embodiment of the invention.

The aperture stop 450 is an example of an aperture stop that is not spiral and differs from an approximation of a spiral.

Aperture stop 450 includes three openings 461, 462 and 463. It is noted that opening 463 and 462 may be combined and that aperture portion 465 (see FIG. 15) can be separated from other portions of aperture 462.

Aperture stop 450 has an axis of symmetry 492 and an axis of asymmetry 491. The symmetry is an approximated symmetry—as aperture 463 and aperture portion 465 differ from each other by their relationship to aperture portion 455.

Aperture stop 450 was also designed to inspect defects that are expected to be oriented along the X-axis and/or the Y-axis (corresponding to orientation of zero and ninety degrees).

Aperture stop 450 passes more (attenuates less) reflected signals at angular deviation (in relation to specular reflection) of 1-5 degrees—in relation to aperture stop 410.

Circular region 459 of aperture stop may be formed of an interior circular portion 452 and an exterior ring 451 that surrounds the interior circular portion 452.

The various openings and/or opening portions that are located within interior circular portion 452 are referred to interior openings and/or interior opening portions respectively.

The various openings and/or opening portions that are located within exterior ring 451 are referred to exterior openings and/or exterior opening portions respectively.

Opening 462 has linear edge portions 4621, 4623, 4625, 4627, 4629, 4651, 4652, 4653, 4654, 4656 and non-linear edge portions 4622, 4624, 4626, 4628, 4655 and 4657.

Linear edge portions 4621, 4652 are parallel to the axis of asymmetry and are scant lines of interior circular region 452.

Linear edge portions 4623, 2625, 4627, 4629, 4654 and 4656 are parts of imaginary diameters of aperture stop 450.

Linear edge portions 4651 and 4653 are oriented (by less than ninety degrees) to the axis of asymmetry and are not a part of any diameter of aperture stop 450.

Opening 461 has linear edge portions 4611, 4613 and 4615 and non-linear edge portion 4614.

Linear edge portion 4611 is parallel to the axis of asymmetry and is a scant line of interior circular region 452.

Linear edge portions 4613 and 4613 are parts of imaginary diameters of aperture stop 450.

Linear edge portions 4612 and 4616 are oriented (by less than ninety degrees) to the axis of asymmetry and are not a part of any diameter of aperture stop 450.

Edge portions 4614, 4624, 4629 and 4655 may be a part of the exterior edge of exterior ring 451.

Edge portions 4622, 4651, 4653 and 4657 may be a part of the interior exterior edge of exterior ring 451 which is the exterior of the interior circular portion 452.

FIG. 36 illustrates five opening points 471, 472, 473, 474 and 475 and their corresponding opaque points 476, 477, 478, 478 and 480.

Each pair of opening point and corresponding opaque point are positioned on a diameter of aperture stop 450—at the same distance from the center of aperture stop 450—and at opposing sides.

It should be noted that the axis of asymmetry and axis of asymmetry can be oriented in other manners (for example— not oriented in 45 degrees and/or −45 degrees). The orientation may be set according to the expected or actual orientation of the detects of interest.

Those skilled in the art will recognize that boundaries between the functionality of the above described operations are merely illustrative. The functionality of multiple operations may be combined into a single operation, and/or the functionality of a single operation may be distributed in additional operations. Moreover, alternative embodiments may include multiple instances of a particular operation, and the order of operations may be altered in various other embodiments.

Thus, it is to be understood that the architectures depicted herein is merely exemplary, and that in fact many other architectures can be implemented which achieve the same functionality. In an abstract, but still definite sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

However, other modifications, variations, and alternatives are also possible. The specifications and drawings are, accordingly, to be regarded in an illustrative rather than in a restrictive sense.

The application is not limited to 2D and may expand to 3D inspection. The inspected substrate is not limited to a wafer and may include any type of substrate, especially flat substrates such as a printer circuit board, a solar panel, a MEMS device and the like.

The word "comprising" does not exclude the presence of other elements or steps then those listed in a claim. It is understood that the terms so used are interchangeable under appropriate circumstances such that the embodiments of the invention described herein are, for example, capable of operation in other orientations than those illustrated or otherwise described herein.

Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe.

Thus, these terms are not necessarily intended to indicate temporal or other prioritization of such elements. The mere fact that certain measures are recited in mutually different claims does not indicate that a combination of these measures cannot be used to advantage.

We claim:

1. An inspection system for inspecting a semiconductor substrate, that comprises:
    an inspection unit that comprises a partially blocking bright field unit and a non-blocking bright field unit;
    wherein the partially blocking bright field unit is configured to (i) block any specular reflection that fulfills the following: (a) the specular reflection is caused by illuminating, along a first axis, of an area of the wafer, (b) the specular reflection propagates along a second axis, (c) the first axis and the second axis are symmetrical about a normal to the area of the wafer, and (d) the normal is parallel to an optical axis of the partially blocking bright field unit; and to (ii) allow transmission, through the partially blocking bright field unit, of some other specular reflected beams; and
    wherein the non-blocking bright field unit is configured to pass to the image plane any specular reflection that fulfills the following: (a) the specular reflection is caused by illuminating, along the first axis, of an area of the wafer, (b) the specular reflection propagates along the second axis, (c) the first axis and the second axis are symmetrical about the normal, and (d) the normal is parallel to the optical axis of the partially blocking bright field unit.

2. The inspection system according to claim 1, wherein the non-blocking bright field unit and the partially blocking bright field unit do not share any optical components.

3. The inspection system according to claim 1, comprising a black and white camera that is positioned in the image plane.

4. The inspection system according to claim 1, wherein the partially blocking bright field unit comprises a partially blocking aperture stop.

5. The inspection system according to claim 4, wherein the partially blocking aperture stop is positioned in an objective lens exit pupil plane.

6. The inspection system according to claim 1, wherein the partially blocking aperture stop comprises first type segments and second type segments that differ from each other by polarization.

7. The inspection system according to claim 1, wherein the partially blocking aperture stop comprises first type segments and second type segments that differ from each other by spectral transmission.

8. The inspection system according to claim 1, wherein the partially blocking aperture stop comprises first type segments and second type segments that differ from each other by transparency.

9. The inspection system according to claim 1, comprising a group of aperture stops that comprise multiple aperture stops that virtually form a partially blocking aperture stop, wherein the multiple aperture stops comprises a first aperture stop and a second aperture stop, wherein the first aperture stop is located upstream to a second aperture stop.

10. The inspection system according to claim 9, wherein when the aperture stops of the group when oriented at different orientations form different partially blocking aperture stops.

11. The inspection system according to claim 9, wherein when the aperture stops of the group when positioned at different positions form different partially blocking aperture stops.

12. The inspection system according to claim 9, wherein a first aperture stop of the multiple aperture stops is located in an illumination path and a second aperture stop of the multiple aperture stops is located in a collection path and downstream of an objective lens.

13. The inspection system according to claim 9, wherein a first aperture stop of the multiple aperture stops is located in an illumination aperture stop plane and a second aperture stop of the multiple aperture stops is located in a re-imaged exit pupil plane.

14. The inspection system according to claim 1, wherein the non-blocking bright field unit and the partially blocking bright field unit share at least one optical component.

15. The inspection system according to claim 14, wherein the at least one optical component is a configurable spatial light modulator.

16. The inspection system according to claim 1, comprising an objective changing unit that is configured to automatically replace objective lens that are used during an inspection process.

17. The inspection system according to claim 1, comprising an aperture stop changing unit configured to replace aperture stops used during the inspection process changing the field blocking stops of the partially blocking bright field unit.

18. The inspection system according to claim 1 further comprising a processor for processing images acquired by at least one of the non-blocking bright field unit and the partially blocking bright-field unit.

19. The inspection system according to claim 18, wherein the processor is configured to process the images and detect at least one defect out of inner cracks, bumps defects, epi pillar defects, bonded wafers inner layers defects.

20. The inspection system according to claim 18, wherein the processor is configured to process the images and measure at least one dimension or at least one element that appears in one or more of the images.

21. An inspection method for inspecting a semiconductor substrate, the method comprises:
operating an inspection unit in a first mode, wherein the inspection unit comprise an exit pupil, an illumination module and an image sensor; wherein the operating in the first mode comprise illuminating an entirety of the exit pupil, and receiving by the image sensor light from the entirety of the exit pupil; and
operating the inspection unit in a second mode, wherein the operating in the second mode comprises positioning an aperture stop in the exit pupil thereby preventing the illumination module from illuminating the entirety of the exit pupil, and prevents, by blocking at least one specular reflectance, the image sensor from receiving light from the entirety of the exit pupil;
wherein when operating in the second mode the aperture stop is configured to (i) block any specular reflection that fulfills the following: (a) the specular reflection is caused by illuminating, along a first axis, of an area of the wafer, (b) the specular reflection propagates along a second axis, (c) the first axis and the second axis are symmetrical about a normal to the area of the wafer, and (d) the normal is parallel to an optical axis of the aperture stop, and (ii) allow transmission, through a partially blocking bright field unit, of some other specular reflected beams; and when operating in the first mode the aperture stop is configured to pass to the image plane any specular reflection that fulfills the following: (a) the specular reflection is caused by illuminating, along a first axis, of an area of the wafer, (b) the specular reflection propagates along the second axis, (c) the first axis and the second axis are symmetrical about the normal, and (d) the normal is parallel to the optical axis of the aperture stop.

22. The inspection method according to claim 21, wherein the inspection unit comprises a group of aperture stops that comprise multiple aperture stops that virtually form a partially blocking aperture stop, wherein the multiple aperture stops comprises a first aperture stop and a second aperture stop, wherein the first aperture stop is located upstream to a second aperture stop.

23. A non-transitory computer readable medium that stores instructions for inspecting a semiconductor substrate by: performing a first inspecting session that comprises inspecting a first region of a first semiconductor substrate, wherein the inspecting of the first region comprises (i) blocking, by a partially blocking bright field unit, any specular reflection that fulfills the following: (a) the specular reflection is caused by illuminating, along a first axis, of an area of the wafer, (b) the specular reflection propagates along a second axis, (c) the first axis and the second axis are symmetrical about a normal to the area of the wafer, and (d) the normal is parallel to an optical axis of the partially blocking bright field unit, to (ii) allow transmission, through the partially blocking bright field unit, of some other specular reflected beams; and performing a second inspecting session that comprises inspecting a second region of a second semiconductor substrate, wherein the inspecting of the second region comprises passing to an image plane any specular reflection that fulfills the following: (a) the specular reflection is caused by illuminating, along the first axis, of an area of the wafer, (b) the specular reflection propagates along the second axis, (c) the first axis and the second axis are symmetrical about the normal, and (d) the normal is parallel to the optical axis of the partially blocking bright field unit.

* * * * *